(12) United States Patent
Abramson et al.

(10) Patent No.: US 10,011,883 B2
(45) Date of Patent: Jul. 3, 2018

(54) CAUSATIVE AGENTS AND DIAGNOSTIC METHODS RELATING TO RHEUMATOID ARTHRITIS

(71) Applicants: Steven B. Abramson, Rye, NY (US); Jose U. Scher, Jersey City, NJ (US); Dan R. Littman, New York, NY (US); Eric G. Pamer, Guilford, CT (US)

(72) Inventors: Steven B. Abramson, Rye, NY (US); Jose U. Scher, Jersey City, NJ (US); Dan R. Littman, New York, NY (US); Eric G. Pamer, Guilford, CT (US); Carles Ubeda, Valencia (ES); Randy S. Longman, New York, NY (US); Andrew Sczesnak, Berkeley, CA (US)

(73) Assignees: NEW YORK UNIVERSITY, New York, NY (US); MEMORIAL SLOAN-KETTERING CANCER CENTER, New York, NY (US)

( * ) Notice: Subject to any disclaimer, the term of this patent is extended or adjusted under 35 U.S.C. 154(b) by 520 days.

(21) Appl. No.: 14/351,622

(22) PCT Filed: Oct. 15, 2012

(86) PCT No.: PCT/US2012/060234
§ 371 (c)(1),
(2) Date: Apr. 14, 2014

(87) PCT Pub. No.: WO2013/056222
PCT Pub. Date: Apr. 18, 2013

(65) Prior Publication Data
US 2016/0222436 A1 Aug. 4, 2016

Related U.S. Application Data

(60) Provisional application No. 61/627,627, filed on Oct. 14, 2011.

(51) Int. Cl.
*C12Q 1/68* (2018.01)
*G01N 33/569* (2006.01)
(Continued)

(52) U.S. Cl.
CPC .............. *C12Q 1/689* (2013.01); *C12Q 1/18* (2013.01); *C12Q 1/6883* (2013.01);
(Continued)

(58) Field of Classification Search
CPC ...................................................... C12Q 1/689
See application file for complete search history.

(56) References Cited

U.S. PATENT DOCUMENTS

2009/0155822 A1  6/2009 Bang et al.

FOREIGN PATENT DOCUMENTS

WO        2011053653        5/2011

OTHER PUBLICATIONS

Vaahtovuo, J. et al. The Journal of Rheumatology 35(8):1500 (2008).*

(Continued)

*Primary Examiner* — Diana B Johannsen
(74) *Attorney, Agent, or Firm* — Klauber & Jackson LLC

(57) ABSTRACT

Methods, reagents and compositions thereof for predicting RA onset in susceptible individuals, diagnosing RA onset, and/or evaluating efficacy of a therapeutic regimen for treating RA are described herein. Determining the amount of a particular bacterial species comprising SEQ ID NO: 1, SEQ ID NO: 2, or SEQ ID NO: 3 (SEQ ID NO: 1+ bacteria) serves as a biomarker for the above indications.

16 Claims, 21 Drawing Sheets

(51) Int. Cl.
  *C12Q 1/689* (2018.01)
  *C12Q 1/6883* (2018.01)
  *C12Q 1/18* (2006.01)

(52) U.S. Cl.
  CPC . *G01N 33/56911* (2013.01); *C12Q 2600/106* (2013.01); *C12Q 2600/158* (2013.01); *G01N 2800/102* (2013.01); *G01N 2800/50* (2013.01); *G01N 2800/52* (2013.01)

(56) References Cited

OTHER PUBLICATIONS

Turnbaugh, P.J. et al. Nature 457:480 (Jan. 2009).*
Steven, B. et al. GenEmbl direct submissions of 16S rRNA sequences of multiple uncultured bacteria, 10 pages (Dec. 2009).*
Turnbaugh, P.J. et al, 4 page excerpt of Supplementary Information for Nature 457:480 (Jan. 2009)(including p. 1 and 9-11).*
Martinez-Martinez, R.E. et al. J. Clin. Periodontol. 36:1004 (2009).*
Whittle, S.L. and R.A. Hughes, Rheumatology 43:267 (2004).*
Alauzet C et al (2010) New insights into Prevotella diversity and medical microbiology Future Microbiology 5 (1):1695-1718.
Cox CJ et al (2002) Investigation of infectious agents associated with arthritis by reverse transcription PCR of bacterial rRNA Arthritis Res Ther 5(1):R1-R8.
Eerola K et al (1994) Intestinal flora in early rheumatoid arthritis Br J Rheumatol. 33(11):1030-1038.
Elinav et al (2011) NLRP6 inflammasome regulates colonic microbial ecology and risk for colitis Cell 145(5):745-757.
Hirota K et al (2007) Preferential recruitment of CCR6-expressing Th17 cells to inflamed joints via CCL20 in rheumatoid arthritis and its animal model J Exp Med 204(12):2803-2812.
Ivanov II et al (2009) Induction of intestinal Th17 cells by segmented filamentous bacteria Cell 139(3):485-498.
Lucke K et al (2006) Prevalence of *Bacteroides* and *Prevotella* spp. in ulcerative colitis J Med Microbial 55 (Pt.5):617-624.
Mangat P et al (2010) Bacterial and human peptidylarginine deiminases: targets for inhibiting the autoimmune response in rheumatoid arthritis? Arthritis Res Ther 12(3):209.
Martinez-Martinez RE et al (2009) Detection of periodontal bacterial DNA in serum and synovial fluid in refractory rheumatoid arthritis patients J Clin Periodontal 36(12):1004-1110.
Modi DK et al (2009) Rheumatoid arthritis and periodontitis: biological links and the emergence of dual purpose therapies Indian J Dent Res 20(1):86-90.
Moen K et al (2003) Immunoglobulin G and A antibody responses to Bacteroides forsythus and Prevotella intermedia in sera and synovial fluids of arthritis patients Clin Exp Rheumatol 10(6):1043-1050.
Moen K et al (2006) Synovial inflammation in active rheumatoid arthritis and psoriatic arthritis facilitates trapping of a variety of oral bacterial DNAs Clin Exp Rheumatol 24(6):656-663.
Ogrendik M et al (2005) Serum antibodies to oral anaerobic bacteria in patients with rheumatoid arthritis MedGenMed 7(2):2.
Ogrendik M et al (2006) Treatment of rheumatoid arthritis with omidazole. A randomized, double-blind, placebo-controlled study Rheumatology 45(5):636-647.
Ogrendik M (2009) Rheumatoid arthritis is linked to oral bacteria: etiological association Mod Rheumatol 19(5):453-456.
Routsias JG et al (2011) Autopathogenic correlation of periodontitis and rheumatoid arthritis Rheumatology 50 (7):1189-1193.
Schellekens GA et al (2000) The diagnostic properties of rheumatoid arthritis antibodies recognizing a cyclic citrullinated peptide Arthritis Rheum 43(1):155-163.
Scher JU et al (2011) The microbiome and rheumatoid arthritis Nat Rev Rheumatol 7(10):569-578.
Severijnen AJ et al (1989) Cell wall fragments from major residents of the human intestinal flora induce chronic arthritis in rats J Rheumatol 16(8):1061-1068.
Vaahtovuo J et al (2008) Fecal microbiota in early rheumatoid arthritis J Rheumatol 35(8):1500-1505.
van der Heijden IM et al (2000) Presence of bacterial DNA and bacterial peptidoglycans in joints of patients with rheumatoid arthritis and other arthritides Arthritis Rheum 43(3):593-598.
Wegner N et al (2009) Autoimmunity to specific citrullinated proteins gives the first clues to the etiology of rheumatoid arthritis Immunol Rev 233(1):34-54.
Wu HJ et al (2010) Gut-residing segmented filamentous bacteria drive autoimmune arthritis via T helper 17 cells Immunity 32(6):815-827.
NCBI GenBank Accession No. HM442456 Apr. 18, 2011.
Scher et al., "Periodontal disease and the oral microbiota in new-onset rheumatoid arthritis", Arthritis Rheum, 2012, 64 (10):3083-3094.

* cited by examiner

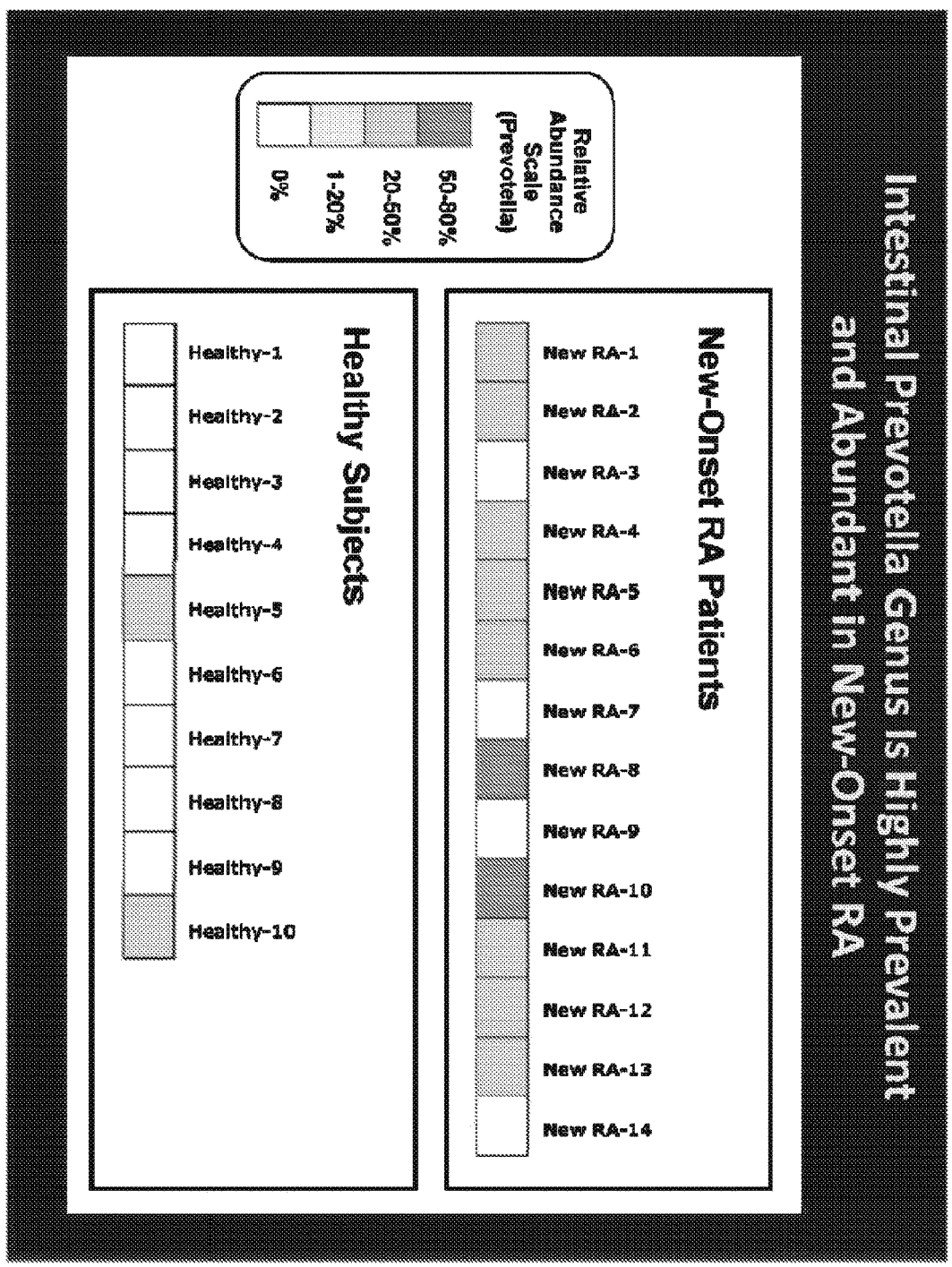

Fig. 4A

GCGAAAGTAAGACTAATGCCCAATGACATCTCTAGAAGACATCTGAAAGGGA
TTAAAGATTTATCGGTGATGGATGGGGATGCGTCTGATTAGCTTGTTGGCGGG
GTAACGGCCCACCAAGGCGACGATCAGTAGGGGTTCTGAGAGGAAGGTCCCC
CACATTGGAACTGAGACACGGTCCA   (SEQ ID NO: 1)

Fig. 4B

>GSXJRPF02H5FKQ   91323

GCGAAAGTAAGACTAATACCCAATGACGTCTCTAGAAGACATCTGAAAGAGATTAAAGATTTATCGGTG
ATGGATGGGGATGCGTCTGATTAGCTTGTTGGCGGGGTAACGGCCCACCAAGGCGACGATCAGTAGGG
GTTCTGAGAGGAAGGTCCCCCACATTGGAACTGAGACACGGTCCA      (SEQ ID NO: 2)

Fig. 4C

>GHL69XQ01BIZFO   64230

GCGAAAGTAAGACTAATACCCAATGATATCTCTAGAAGACATCTGAAAGAGATTAAAGATTTATCGGTG
ATGGATGGGGATGCGTCTGATTAGCTTGTTGGCGGGGTAACGGCCCACCAAGGCAACGATCAGTAGGG
GTTCTGAGAGGAAGGTCCCCCACATTGGAACTGAGACACGGTCCA      (SEQ ID NO: 3)

FIG. 10
Does P. copri Colonization Alter Collagen Induced Arthritis?
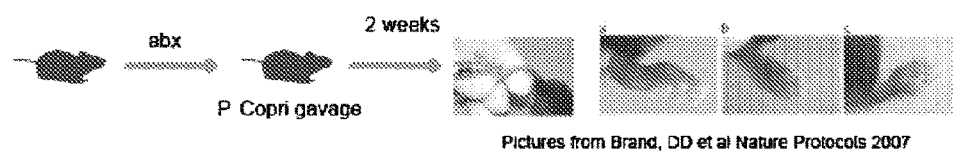
Pictures from Brand, DD et al Nature Protocols 2007
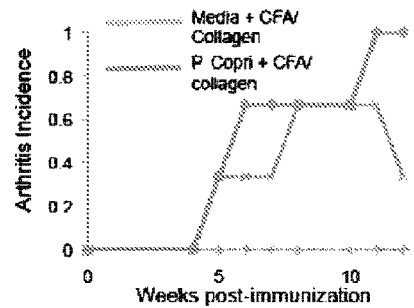
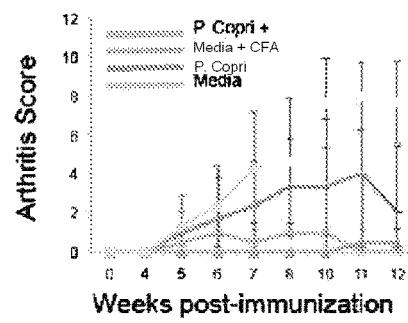
Preliminary data, N=3/group

Figure 11 clust 04539
ATGGACGATGAACGACTCAAAAATCTTGGTGGTGGTAACTATTGGAAAGAGTTGCTCGAC
CGTATTCGTGATATTCGTTCATCAGAAAAGGTGCTTTATCGACAAGTTCTGGACATCTAT
GCCACAAGTGTTGACTATGACCCTCGAACTGATGCCTCAAAGCTTTTCTTTAAAATCGTG
CAAAATAAGTTGCACTATGCTGCTCATGGGCATACAGCGGCAGAAGTTATCTATGAGCGT
GCGGATGCCGACAAACCATTTATGGGCTTGACGACATTTGAGGGCGAACTGCCAGCTATC
AAAGACATCAAAATAGCCAAGAACTATCTGAAAGAAAATGAGCTGAAGATACTCAATAAT
CTTGTTTCCGGTTATTTTGATTTTGCCGAGATTATGGCAATGGAGCATCGCCCAGTCTAT
ATGATGGATTATGTGAAACAACTTGATACTATCCTGCAATCCACAGGGCGACCTTTGTTG
AAGGGGTCGGGAAGTATCAGCCATGAAGAGGCAATGGACAAAGCTATAGCTGAGTATCGA
AAATATCAGGTAAAGGTATTAACTCCAGTAGAGGAGGCTTATCTTGAATCCATCAATGCT
TTGGGAAAAATTGCAAAGCGCAAGGGAAGACAATCGGGGGAAAATCATTAA (SEQ
ID NO: 40)

Fwd: ATGGACGATGAACGACTCAAAAATCT (SEQ ID
NO: 41)
Rev: TTAATGATTTTCCCCCGATTGTCTTC (SEQ ID
NO: 42)

clust03057
ATGGATAAACTCGTAGAGCGAACCAACGGAGCCATCACCAAGCAGAGCATCTCCCGATAT
GAGAAAGGCATCATGCGCCCTAAGCGTGATGCCCTGCAAGCCATAGCCAAAGCCCTCAAT
ATCAGCGAGGAATATTTCGAAGGAACCAATCTCAAGATAGATATGCCTATGCTCCGCACC
ACCTCCAGTGGCAAGTTGTCCGAAGACGAGTTGCAAGCCCTGGAAGCAAAACTCTCGTTT
TGGGCAGAGCAGTATCTTACGAAGGAGAAAGAAGCAGGCTTTCCTACCCGGTTCAAGAAT
CCGGTAAAAGGCACCAAGGTATCAACCCTTGAAGATGCCATCCATGCTGCCGACCTTCTT
CGTGAAAAGTGGTATTGCGGTGATGGACCTATCGCCAGTATCCTGAGACTCTTGGAAAGA
AAAGGTATCATGATACTTGCTGCAACTCTCCCGGATTATGTCTTCGGAATGAGCACCTGG
GCAGATAAGAAGCATCCGCTGATGATTCTCGATTTCAATCCGGAAAAGAGTAGCGTAGAG
AAACTTCGCTTCACGGCAGTTCATGAACTGGCCCATCTGCTTCTCCTCTTCCCGGAAGAT
AGTCCGCTGAGGCTGGAGAAGCGTTGTGATCTCTTTGCCAGTTTCTTCCTTCTTCCTAAA
TTGGCGCTTATCGAAGAGTTGGGTTCCAAGAAACGTGAGAAGATAACGCTGGAGGAGATG
ATTGACATCAAGGAACTGTATGGCGCATCTCTCGCCGCATCCATCATCGCCGCCAGGGAT
TATGGCATTATCACCACCGAGTATAAACGTGCATGGTATGCCGAGCATATAGAGCCTAAT
CCTCGAGAAATAGGTAATGGCCACTATGCATTTCCTGAGACATTGGGAAGGGAGAAGAGA
GTCAACTCAATCATCAAAAGTATGGAGGAATAG (SEQ
ID NO: 43)

Fwd: ATGGATAAACTCGTAGAGCGAACCAA (SEQ ID
NO: 44)
Rev: CTATTCCTCCATACTTTTGATGATTG (SEQ ID
NO: 45)

clust04988
ATGGAGAATGGCGAAGTTGTGACTCGCCCTGAATACCTCATCCTCCCTGCCACCTTCGGC
ATGTGGATGATGGTGATGGTACTCTACATCTTCTCAACCAAGAACGGATGTAACTTCATC
AACTGGTGGCAGCGTGTTCTTTTCCGTTCCAGCAAGAATAAGATTGCCGCCCGTCCGATG
ACACATCATACAAGTATCGTCACCTTCATGGAACTGAACATGATTCTCTGGACCAGCTAT
CTCCTGTTGATGTTCTGCTACGACAAGAATTTCCTCGGCGACCATCACCCTGTAACTTCG

Figure 11 (cont)

GTTGTTGCCGCAGCTTGTCTGATAGGTAGTTTCTTCATCTTCCGAAAGCAGTTGCGTTTG
AGCACATGGGGAGCAAACATCCGTATGGCTATCGCAACGGTTGTCGTGTTCTGGGTACCT
GTGGAAGTGCTTGGTCGCTTGGACTTTTTCAAGGAGATTTGGATTGAGCCAGAGAAGTAT
ATCACCCAGATGATCTGCATCCTCGTGGCATTCGTGGCATTGCTCGTCTATATCATGATA
GTATCTAAAAAGAAGAAGACACATGAGTAA (SEQ ID
NO: 46)

Fwd: ATGGAGAATGGCGAAGTTGTGACTCG (SEQ ID
NO: 47)
Rev: TTACTCATGTGTCTTCTTCTTTTTAG (SEQ ID
NO: 48)

clust01653
ATGAAGTTCTTTGGAAGACAAAACGAAATAAAAGAATTGCAAGAGATAAGAAATCTATCT
TTGCAAACGGCCCGTTTTACAATCGTAACCGGACGCCGACGTAGCGGTAAGACATCCTTA
TTGATAAAAGCATACGAGGATGTTCAGGATATGCTGTATTTCTTTGTTGCAAGAAAATCA
GAAGCAGAACTCTGCAGAGATTTTATCGAAGAGATGACGACCAAACTTCAGCTTCCTATT
CTCGGTGAAGTAACACGCTTTGCTGACATCTTTAAATATCTGCTTCAACTATCCAAGATT
CGCCCTATCACTCTCATCATTGATGAGTTTCAGGATTTCAAGCGGGTTAATCCATCAATC
TTTTCAGATATGCAAAAGATATGGGACCTTAACAAACAGGAAGCTCATATTAATCTTGTG
GTCTGCGGTTCTGTTTATTCACTTATGAACATCATCTTTAAAAATAACAAGCAACCACTT
TATGGCAGGCAGACTGGAGAAATAAAAGTCACTCCATTTCCCCCTTCTGTCATTAAGGAA
ATTCTCTCTACATATAATTCTGCCTATACCAATGATGACCTACTGGCTCTCTACAGTTAT
ACAGGCGGAGTAGCAGAATATGTAGAAATGATGATGGATGCAGGAGCCACGACCAAGGAA
CAGATGACAGAGCGGTTTATTGCAAAAAACTCTTATTTCATCTACGAAGGAAAAAATATG
CTGATAGAAGAATTTGGCAAAGACTATGCCCGCTATTTCGAGATACTGCAACTTATCGCT
TCAGGCTACACAACTCGAGGTGAAATAGAAAGCATCATGAAAATAGAACTTTCGGGCTAT
CTCACCAAACTGGAGAACGACTATAGCTTGATCTCCCGTTATATACCGATGTTCCAAAAG
ACCAATCGCAACATTCGCTATCAGATAGAAGACAACTTCCTTCGCGTCTGGTTTCGCTAC
ATCTACAAATATGGATACATGATAGAGGTTGGCGCCAATAAAAAACTAAAAATGGTCATG
GATAAGAGCTACACCACATACACCGGCAAGGTTCTGGAAAGATATTTTATTGCCAAGATG
ATAGAGAGCGAAGAATATACCCAGATAGCCTCCTGGTGGGACAGAAAGGGAGAGAATGAA
ATCGATATTATCGCTGCCGATGAACTGGAGCAGAAGGTTATTTTTTATGAGGTAAAACGC
CAAGCTAAGGATATAAATCTCGGCATTTTAAAAGATAAAGCCGAGCATTTCTTCCAAGCT
ACAGGAAAATTCAAGAAATTCGATATCGGATACCAAGGATTGTCGATGGAGGATATGTAA (SEQ ID
NO: 49)

Fwd: ATGAAGTTCTTTGGAAGACAAAACGA (SEQ ID
NO: 50)
Rev: TTACATATCCTCCATCGACAATCCTT (SEQ ID
NO: 51)

clust04813
TTGGTAGTAGATGAGAGTGGCAGCATGAGCATTATCGAGCGCCAGGCACTGGTGGGCATC
AACGAGACCCTGACCACGATTCAGAAAATGCAGAAGACGCATAAGAACATGGAGCAGCGT
GTAACGCTCATTACCTTCGACAGCACCCACAAGAAGCTGTTCTACGATAATGTGTCTGCC
CGCCATGCCACCCATTTGACCTCAAGGGATTACAACCCATGTGGCGGCACCCCTCTTTAT
GATGCCATAGGTATGGGTATAGCCAAGATCAATGCCCTGACCACCGAGGATGACAGCGTA

Figure 11 (cont.)

TTGGTAACCATCATTACGGATGGTGAGGAGAACTGCAGCGAGGAGTATGATTTGAAGATG
ATCAAGAACCTCATTGAGAAGCTGAAGAAACAGAACTGGACCTTTACCTTTATCGGCACC
GATGACCTTGATGTGGAAAACATTGCTCTTGATATGGGAATCGACAACCACCTGCAGTTC
TCGGAAGATGAGGCTGGCACCAGGGCGATGTTTGCAAGAGAAAACAGAGCCCGAGAGCGC
TACAACAAGTGCCGTGCGATGGATTGCAAGATGGAAGCTGGGAGTTACTTTGAGGAGAAA
TAA (SEQ
ID NO: 52)

clust00840
GTGAAAATACTACTATTATTTAGACCCCATTTTATTATAAATATAATATATATACCTGAT
AATCAGTTGTATTGTGCTTTTCTGCAGACTTTGTATTTTAGACCCTATTTAGTTCTATTA
TTGAAAAATATTTTGTATTTTTGCGCCCTGAATGTAATTATACTAAATATGAGAAGAAGT
ATTTCGTTTACGATATTGTTTTTTATGATGCTTTCGGTGTTGGTATCATGTTATCAAAGT
CATAAGAGAGAGTTAGACTTAGCTTATACGTTGGCAGAGTCTAAGCCTGATAGTGCCTTG
GCCTTTTTGAACCGTATCAATCAAGGTAAACTCTCAGATAAAGATATGGCGAAGTATGCC
CTCACTTATTATATGGCACAAGACAAGTCTGGCTTAGATGTGGATAACGATTCTTTGATT
CGCATAGCGTATGATTGGTATGGAGAACATCAGGACGATTCTCTTTATGCTTCATCCTTG
TATTATATGGGAAAATGCTTTCTGCTGAATGATAGTATGGAGCAGGCTAAGGCATGTTTG
GAGAAATCTTATTCTATTTCAGACAGTCTTCATAATCTGAGCTTAAAATGCTTGGCATTG
GATAAGCTGATAGAAGTAGAAGAACAACTGGCACCTTACAAAGCGTTGAACTATGCTAAA
GCTTTGGTGAAGATGTATGAGTCCATGCCAAATGTTAGTATATATAATAAGGTGGCAGCG
CATTTGAGGTTAGGGGAGAACTTCTTTTATGTTGATAGTTTGAAACAAGCTTTGAACGAA
GAGAAAAAGGCATATAGGTTGGCGATATATGCAAACGATAATGAATTGCTGTCAAGTGTA
AAACAAAATTTGGCTAGTACGTTTGAGGAAATGGGAGAAAAGGATAGTTGTCTGCTTTAT
GCTCAACAAGCCTATGGGTTACAAGGTGCAAGTAGTTTTTCTTGTCAACTAAATCTAGCC
TTGGCTTATATTTCTGTCGATTCTATAAAACAAGCTTTTGTCTTGTTGGATCAAGCAACT
CCTAAAACTGCTGAAGATCATTATTCGATATTTTATATGAAAAGTAAAGCAGCTATGAAA
GCTCAAGATTATAAGATGGCTAAAACCTTTAGTGATTCTGCATGTTGTTACTTGCAAGAA
ATGTACCGAACAGCATCCAAAGCCAAGATTTCCTATTACACTTCATTCTTGAAGAAAGAA
AGCGAAAGGGCAAGAATACAAGGTAAGGCTGAAATGCAGCGATGGGTATTTGGATTGACA
GTACTTTTATGCTTGATAATTATTTTGTTTGTCTTGTATGCTTATTGGTCGTATCGAAAA
CTGTCATTAGCTCGCATAGCTCATGAACAGGAAATATTCACCCAAAAGCAGCAAATGATG
GAGAAATTACACCAAGAAGAACTCTCGCATAGGGATGTGCAATTGTCTGTAATGCGTACC
TATTTACTAAAGAAGATAGAGGTTGTGGAAAAATTAAATTCGAGTGTTCCGAATGAGAGT
AAGCATATTGTGCTTTCCGATAATGATTGGACAGAGTTAGAAGTCTTCTTAGATAGTGTG
GAGGATTTGTTTGTGTCTAGACTAAAGAAAGAGCATCCTAATTTGTCCAATGCTGACGTG
CGATTAATGATGCTGTTGCGTTTAAAGTTATCGCAAAAGACTTTAGCATCTATCTATTGT
GTGAGCGAGAAAGCTATCAAGCAAAAGTTGTTCTTGTATAAGGATAAAGTAGGCATTAAA
AATGAGCATTTTTCGCTTCGTAACTACATAGAAAACTTCTAG (SEQ ID
NO: 53)

clust01463
ATGCAGAATGAAAGTCAAAATATAGAATATAAGGAATCATGGCGTGATGAATATCTGAAA
TGGATATGTGGTTTCGCCAATGCCCAAGGTGGACGTATTTATATCGGTGTAAACGACCAG
AAAGAAGTAATCGGTTTATCTGATGCCAAACGATTGTTGGAAGATATTCCTAACAAGATA

Figure 11 (cont.)

GTTAATTATCTGGGCATCGTAGAAGATGTAAACCTTCTTATGGAAGGTGATAAAGAGTAC
ATAGAGATTGTGGTCTCACCAAGTAATATGCCGATAGCCTATAAAGGTACGTATCATTAT
CGTAGTGGTTCTACCAAGCAAGAACTCAAAGGGCTTGCTTTGCAGCAATTCATTATGGAG
AAGATGGGTCATTCATGGGACGATATTCCTGTTTATGGTGCTACTCTTGATGACATAGAC
CGTAATGCGATTGACTATTTTTTGCAATGTAGCATCAAGGCAGGTCGTATGGATGAATCA
GAGACTAATTCGTCGACCGAAGATGTATTGCGTAATCTTGGCTTGTTTACCAGGGAAGGT
GAATTGAAAAATGCTGCCATCTTGCTTTTCGGAAAGCATGTTGGTCAGTTCTTCCCATCT
GCGGTATTCAAGATAGGACGTTTTCATACAGATGAGAGCGATTTGATTATTCAGGATGTG
ATAGAAGGCAACCTGATTCAAATGGCAAGTCGAGTGATGGAAGTACTCCGAACCAAGTAT
CTGCTTTCGCCTATTCACTATGAGGGATTGCAGCGCATAGAGCAGCTGGAGATTCCTGAT
AAGGCATTACGAGAGTTGATATACAATGCCATTTCGCATAAGGCTTATACCGGCCCTGCC
ATCCAGATGCGTATCTACGACCGCAGTATAGAATTGTGGAATTATGGATTGTTGCCAAAA
GAGTTGACTCCTGCAGCTTTGTTGCAGAAGCATTCTTCTTATCCTCGTAACCATAATATT
GCCAATGTTTTTTACAAAGCAGGCTTTGTGGAGTCATGGGGACGTGGCTTCAAGAAGATT
GCCGAGGAGTTTGAACGTGCCAGCTTGCCATTGCCAACAATAGAAGAAAATGGAGGTGGC
GTGATGGCGATAATTCAACGAAAGACGGTAGATGACGTTATCGCAGCGCGTGACGGGAAT
GTCGGTAATATGTCGGTAACAAATGTCGGTAATGTGTCGGTAAGGAAACTGTCTGGTCGT
CAGCGAAATATCATTTCTATGATTGAGGAAAATCCTTTTGTAACAGCTAAGGAAATGTCG
GTAACAATGTCGGTAACGAAACGTACCATAGAACGTAATTTGTCTGTGTTGCAAAAAGCG
GGAATAATAAGGCATGAAGGAAGAGTGAATGCCGGTGTTTGGGTGATACTTGAACAAGGA
AATATGAATTCTTAA (SEQ
ID NO: 54)

Fwd: ATGCAGAATGAAAGTCAAAATATAGA (SEQ ID
NO: 55)
Rev: TTAAGAATTCATATTTCCTTGTTCAA (SEQ ID
NO: 56)

clust02547
ATGAGACAGGCAATATTGGTAGAACCAAAGCATATCGAATTCAAGGAAGTAGCAGAACCA
AAGGCAGCAGACTTAACTGCTCATCAGGTTCTCGTCAACATCAAGCGCATCGGCATCTGC
GGTAGCGAGATTCACTCTTACCACGGTCTTCACCCAGCCACCTTCTACCCAGTGGTTCAG
GGACATGAGTACTCAGGAGTGGTTATGGCTGTAGGCAGCGAAGTTACCGTCTGCAAGCCT
GGCGACCATATCACCGCTCGCCCACAGTTGGTTTGCGGCAAGTGCAACCCTTGCAAGCGC
GGACAGTATAATGTTTGTGAGCACCTGCGTGTTCAGGCTTTCCAGGCAGATGGTGCAGCA
CAGGATTTCTTTGTAGTAGATGACGACCGCGTGGCTAAGTTGCCGGAAGGCATGAGCCTT
GACTACGGTGCCATGATTGAGCCTTCAGCCGTTGGTGCCCATGCCAGCAACCGCACCGAT
GTGAAGGGTAAGAATGTAGTTGTGAGCGGTGCAGGAACCATCGGCAACCTCATAGCCCAG
TTCTGCATTGCCCGTGGCGCCAAGAATGTACTCATTACCGATGTAAGCGACCTCCGCCTG
GCTAAGGCTCGCGAATGCGGCATCAAGCACACCCTCAACATCACCAAGAAGACCTTGAAG
GAGGCAGCCCAGGAACTTTTCGGTGAGGAAGGCTATCAGGTAGGTTTCGAGGTAGCAGGT
GTAGAAGTTTCCATCCGTTCGCTGATGGAGACCATCGAGAAAGGTAGCGACATCGTGGTT
GTGGCAGTCTTTGCCAAGGACCCAGCCCTCAGCATGTTCTATCTGGGCGAGCATGAGTTG
AGACTCATCGGTTCAATGATGTATCGCCACGAAGATTATCTCACAGCCATCGATTACGTA
AGCAAGGGCATCGTCAACCTCAAGCCACTCGTAAGCAACCGTTTTGCCTTCGAAGAATAC
GATGATGCCTACAAGTTTATCGACACTCATCGCGAAACCAGCATGAAGGTTCTCATCGAT
TTCGAACAGAAACCTGGAGAGAAGAAGTAA (SEQ ID
NO: 57)

Figure 11 (cont.)

Fwd: ATGAGACAGGCAATATTGGTAGAACC (SEQ ID NO: 58)
Rev: TTACTTCTTCTCTCCAGGTTTCTGTT (SEQ ID NO: 59)

clust04026
ATGAAAAGAATTGTAGTTATTGTTTTGATGATGGCTGCTTGCCTGGGAAATGCCCAGGCA
CAGCTCCATCTGAAAGCCAACGTGCAGAACAATCATCTGTGGCGTGGCATGGAAGTTTCC
GACGGCATCGTCCTCCTCACCGACCTGAGCTATACGATGGCCAATGACCACGTTACCGTG
GGACTTTGGGGTGGCTGCAACTCGGAAGGCTCCTACAAGGAGTTTAATCATTATCTGAAT
CTGAAGGCTGGCGGTTGGGGATTCGCCCTGTGGGACACCTACAACTTCTCCCCTGGCGCC
AGCTATAATAATAAGGAATACTGGAACTACTCTGCTCATACCACCGGCCGATTCCTCGAT
GCTACATTAAGCTACCGGTTTCAGTACGAGAAGTTTCCACTGCTCCTGAGTTGGTCAACG
GTAGTCTTCGGACGCGACCGCAACAGCAACAACACGAAGCAGAAATATTCCACCTTCGCC
TATGCGGAATATCCTATCTATCAGAAGGATGGCTGGAAGGTAGATGCAGGAGTTGGTGGA
GCCTTCGCCCTGAACAGAGCTGGCGAGGATGCCCACTTCTTCGGAACCACGGCAGGCATC
GTTCACGTATCGCTGCAAGCCACCCACGACCTCAAGCTCGGCAACTACACCGTTCCGGTT
TATGCCAAGGGCATGTGGAATCCGCAGAGCAACGAGAGTTATTTCCAGATTGGAGCAGAA
ATCATCCGCTTCTAA
(SEQ ID NO: 60)

Fwd: ATGAAAAGAATTGTAGTTATTGTTTT (SEQ ID NO: 61)
Rev: TTAGAAGCGGATGATTTCTGCTCCAA (SEQ ID NO: 62)

clust00223
TTGTATAATTTTAAAAAAGAAAAATTTATGAAGAATCAGTTTTGGGGATTATTCCTTCTC
TCTTTGTTTCCAGCTTCATTGTTCGCTCAGACTGTGGAGCAGGACACTTCCGTGCGACAG
GGCAAGTTGAAGAATGGACTGACTTACTATATACGACATAATAATAAAGAGGCAGGCCTT
GCCGATTTCTATATTGCCCAGCGCGTAGGTTCCATCCTTGAGGAACCCCGTCAGCGTGGA
CTGGCTCATTTTCTGGAGCACATGGCTTTCAATGGTACCAAGCATTTCCCTGGCAAGGGG
AAGAAGTTGGGAATCGTGCCTTGGTGTGAAACCATAGGTGTCAAGTTTGGAGCCAACCTG
AATGCCTATACATCTGTAGATCAGACAGTCTATCACATCGGGTCTGCCCCTGTCAAGCGT
GAGGGCATTATTGATTCGTGTCTTCTGGTACTCAACGACTGGAGCCAGTATATCAATCTC
GAACCTAAGGAGATAGACAAGGAACGTGGTGTTATTCATGAAGAGTGGAGAAACCGGCGT
ACCGGTATGGCCATGCAGCGCATGATGGAGAATGTGATGCCAAAAATCTACAAGGGAAGC
AAATATGAAGATTGTATGCCTATCGGCAGTATGGATGTTGTTGATAACTTTCCTTACAGA
GATTTGCGCGACTATTATCAGAAGTGGTACAGGCCTGATCTTCAGGCCATCGTAGTTGTG
GGCGACTTCGATGTGGATATGATGGAGAAGAAAATCCAGAAACTTTTCGGTAAGATCAAA
GCCCATAAGAATCCTGCAGAGCGTGTCTATTATCCCGTAAATAACAACGACAAGATGATA
GTTGCCATTGAGAAGGACAAGGAGCAGCCTATTATCATCGGCCATCTCTACATGAAAACC
GATGCCACTCCTGACAGCGAAAAGAGCCAGGTAAAGTATCAGCGTGATGACTATGTAAGC
GGACTCATCACTTACATGCTCAATGGCCGTCTCTCAGAAAAGAAACAGGTGGCAAATCCT
CCATTCATGAGTGCTACCGTAAGGAATGGTGCTTTTTTTTGTTTCCCGTACCAAGGATGCC
TTCAGTATGAGCATCAGCTGCAAGCAGGATCACGTACTCGGTGGTATCTACGAGGCTGTG
GGTGAAATAGAGCGTGCCCGCCAGCATGGTTTTACAGAGAGTGAACTGGAACGTGCCAAG
AAACTCTATCTCAATGCAGCAGAACGAAAACTGAAGATGGAGAAGGATTATCGCAACGCC

Figure 11 (cont.)

CATTACGTAAGCCAGTGTGTGGATCATTTCCTTGAAGGAGAGCCTATCCTTACTCCAGCC
TATAATCTGCAACTGGTAAAGCAGTTTGATGGTGAAGTAACCCTGGCTGAGGTTAATCAG
TCTGTAGGTAACATCATTACGGATAAAAACCAGGTATTTGTGATGTATGGCCCTGATAAG
GAAGGATTTGTTATTCCTTCAGAATCAGAAATAGAAGCTACGGTACTTGCTGCCCAGAAA
AAGCAATATGAACCGTATCAGGAGGAAAAGATTCCTTCTACGTTGATGTCTGCCTTGCCA
AAACCGGGCAAGATTGTGTCTGAAAAACCATACGGCAAGTTTGGGATGACAGAGATTACG
CTCAGTAATGGTATGAAGGTTTACGTAAAACCTACCGACTATCAGGCAGACCAGGTAATG
ATGAGCATGCGCGCTGAAGGTGGAACCTCACTTTACGGAAATGAGGATATTCCTAATTTC
TCTCTCTTGACAAGTGCCATCACAGAAGCGGGTGTAGGCGACTTTTCAGCTACTGCTTTG
CGTAAGGCTTTGGCAGGAAAGTCAATCAGGCTGACTCCATCCATCAGTAGTGAAGGCCAG
CGTATAGCAGGCTCATCTTCTGTAAAGGATATGGAAACCATGCTCCAGCTGGCACACCTT
TATTTCATGGCACCCCGTAAAGACAGTGTGGCATTTGAGGGTTTGAAGAATCGAACGCTG
TCATTTCTGAAAAACCGTAATGCAAGTTCCAAGGTGGTTTACAATGACTCCCTTTCTGCC
GTTCTCTATGACCATAACCTGCGTATGGCTCCTGTCACCGGTGAGGTTCTTGCCAAGGCT
GATTACGGGCGCATTATGGAAATCTATCGTGAACGCTTCAGCGATGCTAGCAATTTCAAA
ACCGTTTTCATCGGAAAGATAGACATGGCAGAACTTCGTCCTTTACTCTGTCAGTATCTG
GCTACCTTGCCTTCGACCTATAAGAAGGAGGAGACAGACAAGAAAAACGTTCCGCAGATT
GTTATGAAGAACGAAACGGTGAAGTTTGTTCATCAGCAGGAAACACCGCTTGCCAACGTG
AGCGTGTTCTATACGGGCAACGTACCGTTCTCACCAAAGAACGATCTGGTGCTGGATGTC
CTGACCCGCGTATTGCAGATAGCCTATACAGATTCTGTAAGAGAGGAGAAGGGAGGTACC
TATGGAGTAGGAGTCAGTTTCAACCTTGAGAAGGATGCCCTTCCAAATGCCTTACTTCGC
ATTACCTACAAGAGTGATCCGAAACGTTATGAAGAACTGAATCCTATTATCTACCAGCAA
CTTCAGAACATCGCAGATAAGGGGCCTTTAGCCAGCAGTATGGATAAGGTGAAGAAATAT
CTGAAAAAACAATACCAGCAGATGATTATCACCAACGACTACTGGAGTTATGTTATCTGG
CATGAGTTGGATGATGATGCCGATTTTGATAAAGATTACTATAAGATGGTGGATTCTCTT
ACTTCTGAAGAGGTGCAGCAGATGGCACAGACTCTGCTCAAACAGAATCATCGGATAGAG
GTAACAATGCTGTCTGAGTAA (SEQ ID
NO: 63)

clust05565
ATGAAGGTAAAGAATAGTAGAATGGAAACCCTGAAGATGCTTATCTCAAGTCAAGAGTTA
AGTTCACAGGAAGAAGTTTTGAAGGCCTTGTCAAAAGAAGGTTATAAGCTTACGCAAGCC
ACTTTAAGCCGCGACTTGAAACAACTGAAAGTTGCCAAAGCCGCCTCTATGAATGGTAAA
TATGTATATGTACTCCCTAATGAAACCATGTACAAGCGAGTTTCCAATCCTCGTTCGCTC
AAAGAAATGATGATGACCCCAGGATTTCTATCCATCAACTTTTCTGGAAACATGATTGTC
ATCAAGACTCGTCCGGGTTATGCCAGCAGTATTGCATATAACATTGACAATCATGACATT
CCTGAAATCTTGGGTACAATTGCTGGAGATGACACGATTTTCCTGGTAAAGAAAGAAGAT
GCTTCTGAGGAAGCACTTCTGAAATCACTCGCAAATGCCATTCCAGAACTGAAGTAA
(SEQ ID NO: 64)

Fwd: ATGAAGGTAAAGAATAGTAGAATGGA (SEQ ID
NO: 65)
Rev: TTACTTCAGTTCTGGAATGGCATTTG (SEQ ID
NO: 66)

Figure 11
(cont.)

clust06216
TTGAAGAGGCTTCAGAAGCACCGGCTTCCAAAGCACCAGTTTCAGAAGCACCAGCCTTCA
AGCCAGCAGTTTCCAAAGCACAACCATCAGCTCCGAAATCCTGCAGTCTGCAGCATTCTA
TTTCCACCCTGTCGCGAAACGGNNNNNNNNNNNNNNNNNNNCTCTATCTCAAACTGTTTA
AATCGAAAATTACCCATAAATTCTTCTGTCTCTTTACAGAAGAAAACGAATGCGCCGCCG
ATTTATTTTATCGCAAGCAGCAGAAATTGCCACTTCCACCTGCAAAAGCAGCTACTTACA
TCTATAAAAACGGGTACTAAATATATAGAAAAAGCAATTTTATTATTAAATAATCTATCA
TCTTCCACGATATTTCACAAAAAATGA
(SEQ ID NO: 67)

clust06371
ATGACCCGGTATCTTGCGGGCTTTCTTACCCGATACCCTACTGTACCGTCCATCCTCCTC
TTCCGGTTTCAGTTCGATACCCAGGAGGTTTCTCCACGTAGGCTCCAGGGTATCACAGAA
GTAATGCTCCTTGTCCAACTTCGCCATATCAAAGCTGTGCTCAAAGATACGCTTGTCGCC
AATTTTCACACCCGAACGCCAGGTACGCTTCACGTCCTTATCACTCAGGATATAAAGATG
ACCTATCGTATAAGTCTTCTTTTTTGCTATTCTTTTTACTACTATTTCCATAACTCAAAC
TCTATTAAGATTCTAAAATTTTTACCTCTTTACCATCCTTGCGGTTACGTAGCTTTTCAA
AACTGA
(SEQ ID
NO: 68)

Fwd: ATGACCCGGTATCTTGCGGGCTTTCT (SEQ ID
NO: 69)
Rev: TCAGTTTTGAAAAGCTACGTAACCGC (SEQ ID
NO: 70)

clust04469
GTGCAAACGTTTGCACAAAGAAATGTAGCCTTTTTGAAACTTTTTCTTGCTTCNNNNNNN
NNNNNNNNNNNNNNNNAAAAGTAAAGATATGATGAAGCAAACATTCATAAAATCAGCAATG
TTGCTGCTGCTGATCCTTTCAACGGCAACGACGCGAGCGCAGGAGGTCGCTCTGAAGACC
AACTTACTGGGATGGGCTTCTACATCTGCCAACGCCGGCATAGAAATCGGCACGGGCAAG
AAAACAACCTTCCAACTCTTCGGAACCCTGAACCCCTGGAAGTTCTCGGGCGACAAGAAG
ATGAGATTCTGGAATGTTATGCCAGAATACAGATGGTACACCTGCCAGAAGTTTGGAGGC
CATTTCTTCGGAATCCATGCCTTAGGCGGTGAATACAACATTAAAAACATTGACATGCCC
TTCGGCATCCTGCCGAAAACTCTGGAGGGCAGGCACTATGAAGGCTGGTATGTAGGTGGA
GGCCTTACCTACGGCTATCAGTGGTTGCTTAATAAGCACCTCAATTTCGAAGGCTCTATC
GGTTTGGGATATGCCTACAGTCCTTACAAGCTTTACGGACGATGCGAAAAATGTCTCGAC
AAAGACCACCGCAACTATGTGGGCCCTACAAAAGCCGCACTATCTCTCATATACGTGTTC
TAA (SEQ
ID NO: 71)

clust05048
ATGGAAATAGTAGTAAAAAGAATAGCAAAGAAGAAGACTTATACGATAGGTCATCTTTAT
ATCCTGAACGATAAGGATGTGAAACGTACCTGGCGTTCAGGGGTAAAAATAGGCGACAAG
CGTATCTTTGAGCACAGCTTCGATAAGGCGAAGTTGGACAAGGAGCATTACTTCTGTGAT
ACCCTGGAGCCTACGTGGAGAAACCTCCTGGGTATCGAACTGAAACCGGAAGAGGAGGAT

Figure 11 (cont.)

GGACGGTACAGCAGGGTATCGGGTAAGAAAGCCCGCAAGATACCGGGTCATACGGCGATA
CCGGAAGGCTCGTATCCTGTTGTTATCTCGAAATCGCCAAGGTTTAAGAAGTGGCTTCCG
CTGGTGCAGGGTGTTCCTGATTTTGAGGGCATCCGCATTCATGCCGGTAATTATCCTGAT
GATACGCAGGGCTGCATTCTGGTAGGTGAAAATAAATTACAGGGTGCCGTCTTTAATTCC
CGCATCTGGCTGCACAGGCTCATGAATGCCATTACCGCAGCAAGGGAACGGGAGGAGAGC
GTTTGGATTACAATCATTTAA (SEQ ID
NO: 72)

Fwd: ATGGAAATAGTAGTAAAAAGAATAGC (SEQ ID
NO: 73)
Rev: TTAAATGATTGTAATCCAAACGCTCT (SEQ ID
NO: 74)

clust05075
TTGCTGGCATCCCTGTTGCTGATGCTCGTAGCGACGCTTACTTCATGCGAGAAGTTTTCG
ATTGACGAAACAACCGGAAAATCACATGATGCAAACGCCAATGTAACGATTCATGTGCAG
AAAGTAGAAAACACCAATCTGTTGACGACCAAAGCTGCCGACAAGCAGATTGCCCTGGGC
GATGTGTGCTCCAGACTGANNNNNNNNNNNNNNNNNNNNNNNNNNNNNNNNNNNNNNG
CTCTATCAGCGCACCCGAGAAGGTGAAGTTTGCAAGCAACAAACTTACCGACACCTTTTA
TTATTACGGCAGGTTGAGCGTAAACGAAGAGGGCGCCACCACAGACATCAACCTGAGGCG
AGCAGTTGGCGCCTTCAAGGTACATATTACCGACGAAAACATTCCCGAAGAAATCAGGAG
CATCAAGTTCTATTATACCGGCGGCAGCAGCACCCTGGATGCAACCACCGGATTCGGCTG
CGTGAACAGCCGTCAGACCGAGAATTTCAGTATGAAAGATGGCAGCAGAGACTTTACCGT
CTACACCTTCCCACATGA
(SEQ ID NO: 75)

clust05613
GTGGCTTCCGCGTACGAAATCAGCCATCTCCAGGTTCTCTATCAGATTAGGCGTAATCTT
CATGATTTCGTTCTGATGAGAAGCACGGAAGTTGATGTCGTAATAAAGAATGGCGCCGTG
CTCCTTCGCATACTCCAGGAAGCCGGCAACCTGAGGACGGACCACAGGATTCAGAGCGAA
GAACGAACCGAAGAGCACGATGTCGCCAGGATTGATTTCCGGTGTGGCAAACTCCAGCTG
GTCGTGAGGATGATCCTTGTAGAAGATGTAGTCGGCATTGTTGTTCTCGTCGAGGAAAGC
CAGCGAGAGCGGCGACTTCGATTCCGGAAAGATGCTCACATTGTCAGCATTCACCCCATT
ATCTCTCAAAAACTGAATCACATACTCTCCTATGCGGTCGTTGCCCGCCTCGCTGATAAA
CGAAGCATTTACACCCGCACGGCCCAACGAGATGACTGCATTGAATG
(SEQ ID NO: 76) A clust05637
ATGCAGGGCACAGAGCGAGCGGTTCAGCTCCTGGGCTGTGATACCGAGTTCCTTCGCAAT
CTGCGTAGTAGTGAAGCAGGAAACGGAATCGAGCACGTTATCGCTNNNNNNNNNNNNNNN
NNNNNNNNNATCGGCCGTAACCCAGTTCTTGAACTTCACGGCAGTAGAAAGCTTAGAGCC
GAGAACCAAAGCATAGAAACCGCTCTCGTTGACATAGAGCATCAGAGTACGACGCATCGC
CGAGGTTCCATCCTTCTTCAGACCNCAGCATCATTCGCTCTCTTATATCCCAGTACATTA
CAGAGATCCTTTGCACAGAACAATGGCTCCCCATTTTCATCGGTCAAGGTACGAACCTTA
CCGAATTCTGATTTTTCAAACACGACAGCAATTGCTGCCTTCTTATCCATTTCTACTTTA
TTTGTATTAACTGACTTTACCATAATAATCTTTTTAAAAAAATAA (SEQ
ID NO: 77)

Figure 11 (cont.)

Fwd: ATGCAGGGCACAGAGCGAGCGGTTCA (SEQ ID
NO: 78)
Rev: TTATTTTTTTAAAAAGATTATTATGG (SEQ ID
NO: 79)

clust06358
ATGATATTTCTCATCGCCCCTTACAACCACCGTATCACGTTTAATCAGCGTATTCTGATT
CAGCGCCACGGAAGCATGGTTGTGGATGAACTGCTGCAAATAAGACTTATCTTCCGTCTT
CACCAGCTTAACCACATCCCCATTCTGCACTTTAAACTGGAAAATATGCTCAGCCTGTTT
TACAATCGGATATTTTGCAAGATTAGCACCCTTCATTACAAGCGTATCGNNNNNNNNNNN
NNNNTCACTTCCTGTTGCTTTTCGACCTTCTGCCCACAAGCAACAAGAGTCAAGATACAA
CTGAGCAGCCATAAATTAACTATNNNNNNNNNNGGCCATTTTATTCCGATAGTAGGATCA
TCCCAATGA
(SEQ ID
NO: 80)

Fwd: ATGATATTTCTCATCGCCCCTTACAA (SEQ ID
NO: 81)
Rev: TCATTGGGATGATCCTACTATCGGAA (SEQ ID
NO: 82)

clust06535
ATGCGACAAGAGCGGATAAGTCTTGTTACGCACCAGTTTGACAGGTGTACCTTTGATAAA
CTNNNNNNNNNNNNNNNNCTCCGTAAAACTCTGATGATATCCCGACCTGAACTCCCCTAC
TTCCTGAGCCGTAGGATTACCCACATAGTGAATAGGATAACGGTGCTTCTTTTCGAAGAA
CGGCACCTCGAATGGCAAGATAGAGAAGAGTTCAACGATATCACGTTTAATGCTGCGGAT
CCGCCACTCCTTCCATGCNNNNNNNNNNNNNNNNNNNNNNNNNNNTCCACTAGCCTC
GCCTACTATCAGGTAATACTTCATAATTCAAAATTCTTTAACCAATCATAA (SEQ ID
NO: 83)

Fwd: ATGCGACAAGAGCGGATAAGTCTTGT (SEQ ID
NO: 84)
Rev: TTATGATTGGTTAAAGAATTTTGAAT (SEQ ID
NO: 85)

CAUSATIVE AGENTS AND DIAGNOSTIC METHODS RELATING TO RHEUMATOID ARTHRITIS

CROSS REFERENCE TO RELATED APPLICATIONS

The present application is a National Stage Application which claims priority under 35 U.S.C. § 120 from co-pending PCT Application No. PCT/US2012/060234 filed Oct. 15, 2012, which in turn claims priority under from 35 U.S.C. § 119(e) from U.S. Provisional Application Ser. No. 61/627,627, filed Oct. 14, 2011, both of which applications are herein specifically incorporated by reference in their entireties.

GOVERNMENTAL SUPPORT

This invention was made with government support under RC2 AR059896 awarded by the National Institutes of Health. The government has certain rights in the invention.

FIELD OF THE INVENTION

Diagnostic and prognostic methods pertaining to inflammatory and autoimmune disorders are described herein. More particularly, diagnostic and prognostic methods relating to Rheumatoid Arthritis (RA) are set forth herein.

BACKGROUND OF THE INVENTION

Rheumatoid Arthritis (RA) is a chronic, systemic inflammatory disorder of unknown etiology that predominantly affects synovial joints. RA is, moreover, an autoimmune disease that affects about 1% of the Caucasian population, with a higher ratio of females afflicted (Lee et al. 2001; Lancet 358:903-911). The disease can occur at any age, but it is most common in human subjects between 30 to 55 years old (Sweeney et al. 2004; Int. J. Biochem. Cell Biol. 36:372-378). The incidence of RA increases with age.

Although the cause of RA is unknown, certain genetic and infectious factors have been implicated in RA pathogenesis (Smith et al. 2002; Ann. Intern. Med. 136:908-922). Soluble cytokines and chemokines, such as IL-1β, TNFα, IL-1ra, IL-6, IL-8, MCP-1 and serum amyloid A (SAA), have been shown to be associated with rheumatoid arthritis (Szekanecz et al. 2001; Curr. Rheumatol. Rep. 3:53-63; Gabay et al. 1997; J. Rheumatol. 24:303-308; Arvidson et al. 1994; Ann. Rheum. Dis. 53:521-524; De Benedetti et al. 1999; J. Rheumatol. 26:425-431.

The predominant symptoms of RA are pain, stiffness, and swelling of peripheral joints. Of the synovial joints, RA most commonly affects the joints of the hands, feet and knees (Smolen et al. 1995; Arthritis Rheum. 38:38-43). RA can also, however, affect the spine with devastating results and atlanto-axial joint involvement is common in more progressed disease. Extra-articular involvement is a hallmark of RA, which can range from rheumatoid nodules to life-threatening vasculitis (Smolen et al. 2003; Nat. Rev. Drug Discov. 2:473-488). The disease manifests with variable outcome, ranging from mild, self-limiting arthritis to rapidly progressive multi-system inflammation, which is associated with pronounced morbidity and mortality (Lee et al. 2001; ibid; Sweeney et al 2004; ibid). Joint damage occurs early in the course of the disease as evidenced by the fact that bony erosions are detected in 30 percent of patients at the time of diagnosis (van der Heijde 1985; Br. J. Rheumatol. 34 (Suppl 2): 74-78).

Seven diagnostic criteria recognized by The American Rheumatism Association (ARA) (Arnett et al. 1988; Arthritis Rheum. 31:315-324) are used to diagnose RA. The ARA criteria include: 1) morning stiffness in and around joints lasting at least 1 hour before maximal improvement; 2) soft tissue swelling (arthritis) of 3 or more joint areas observed by a physician; 3) swelling (arthritis) of the hand joints; 4) symmetric swelling (arthritis); 5) rheumatoid nodules; 6) elevated levels of serum rheumatoid factor (RF); and 7) radiographic changes in hand and/or wrist joints. For a definitive diagnosis of RA, the first four criteria must be present for a minimum of six weeks. The RA test measures rheumatoid factor—the IgM autoantibody reactive with Fc region epitopes of the IgG molecule (Corper et al. 1997; Nat. Struct. Biol. 4: 374-381). Although RF is primarily associated with RA, these antibodies can be detected in sera from normal elderly people, healthy individuals, and patients with other autoimmune disorders or chronic infections (Williams 1998) and thus, have low disease specificity.

RA is typically treated with a variety of drugs that can be categorized as follows: nonsteroidal anti-inflammatory drugs (NSAIDs); disease-modifying anti-rheumatic drugs (DMARDs), steroids, and analgesics. NSAID drugs (such as ibuprofen and aspirin) reduce swelling and pain associated with the disease but offer only symptomatic relief. DMARDs include sulfasalazine and methotrexate, as well as biological agents, such as Infliximab, Etanercept, Adalimumab and Anakinra. All of the above therapeutics, however, fail to address the underlying cause of RA.

In view of the above, new methods for use in the accurate diagnosis, prognosis, and/or monitoring of patients with rheumatoid arthritis are urgently needed. Methods described herein address these needs.

The citation of references herein shall not be construed as an admission that such is prior art to the present invention.

SUMMARY OF THE INVENTION

As described herein, the present inventors have discovered that a particular bacterial species comprising SEQ ID NO: 1 (SEQ ID NO: 1+ bacteria) of intestinal origin appears to be associated with and causative of RA in human subjects. SEQ ID NO: 1+ bacteria appears to be a *Prevotella* or *Prevotella* related species of bacteria. More particularly, the bacteria appears to *Prevotella copri* (*P. copri*) or a related species. As shown herein, SEQ ID NO: 1+ bacteria is present at significantly higher prevalence and abundance in the gut microbiome of anti-citrullinated protein antibody positive (ACPA+) new-onset rheumatoid arthritis (NORA) patients compared to healthy individuals or chronic-treated RA patients. The present inventors also demonstrate herein that disease-modifying anti-rheumatic drug (DMARD) naive NORA patients exhibit a distinct intestinal microbiome, characterized by an unexpectedly high abundance of SEQ ID NO: 1+ bacteria. Accordingly, the presence and/or abundance of the SEQ ID NO: 1+ bacterial species in a human subject, particularly in the intestinal tract, can be used as a diagnostic indicator for RA onset, as a predictive indicator for RA onset in susceptible individuals, and as a prognostic indicator for RA patients receiving treatment therefor.

SEQ ID NO: 1 was identified as a particular operational taxonomic unit (OTU). As described herein, sequences were grouped into OTUs using the average neighbor algorithm. Sequences with distance-based similarity of 97% or greater were assigned to the same OTU. Accordingly, SEQ ID NO: 1 and variants thereof, designated herein as SEQ ID NO: 2 and SEQ ID NO: 3, can each be used in methods described herein for diagnostic, prognostic and/or therapeutic applications, as well as compositions and screening assays. Indeed, the term SEQ ID NO: 1+ bacteria may be used interchangeably with SEQ ID NO: 2+ bacteria or SEQ ID NO: 3+ bacteria with respect to the findings presented herein.

In accordance with the findings presented herein, a method for determining whether a subject has new onset rheumatoid arthritis (RA) or is at risk for developing RA is presented, the method comprising determining the amount of a *Prevotella*-related species of bacteria in a biological sample obtained from the subject, wherein the *Prevotella*-related species of bacteria comprises SEQ ID NO: 1, SEQ ID NO: 2, or SEQ ID NO: 3. In a particular embodiment thereof, the subject has a familial history of RA and/or exhibits at least one of the seven diagnostic criteria recognized by the ARA to diagnose RA. The ARA criteria include: 1) morning stiffness in and around joints lasting at least 1 hour before maximal improvement; 2) soft tissue swelling (arthritis) of 3 or more joint areas observed by a physician; 3) swelling (arthritis) of the hand joints; 4) symmetric swelling (arthritis); 5) rheumatoid nodules; 6) elevated levels of serum rheumatoid factor (RF); and 7) radiographic changes in hand and/or wrist joints.

In a particular embodiment of the method, the biological sample is fecal material, biopsies of specific organ tissues, including large and small intestinal biopsies, synovial fluid, and synovial fluid biopsies.

In another embodiment of the method, detection or determination of increased amounts of the *Prevotella*-related species of bacteria comprising SEQ ID NO: 1, SEQ ID NO: 2, or SEQ ID NO: 3 in the biological sample obtained from the subject relative to a control sample indicates that the subject has new onset rheumatoid arthritis (RA) or is at risk for developing RA. In a more particular embodiment, the increased amount is exemplified by the *Prevotella*-related species of bacteria representing greater than 20% of total microbiota in the subject.

The method may further comprise assessment of familial history of RA in the subject, clinical symptoms of RA, ACPA/RF levels, or Th17/Treg levels in the subject.

In a further embodiment of the method, the amount of the *Prevotella*-related species of bacteria comprising SEQ ID NO: 1 SEQ ID NO: 1, SEQ ID NO: 2, or SEQ ID NO: 3 in the biological sample is determined by nucleic acid sequencing. In a more particular embodiment, the nucleic acid sequencing is massively parallel 16S rRNA pyrosequencing.

In yet another embodiment, the nucleic acid sequencing detects 16S rRNA comprising SEQ ID NO: 1, SEQ ID NO: 2, or SEQ ID NO: 3 and the amount of the 16S rRNA comprising SEQ ID NO: 1, SEQ ID NO: 2, or SEQ ID NO: 3 is indicative of the amount of *Prevotella*-related species of bacteria in the biological sample. In a particular embodiment thereof, the primers used for nucleic acid sequence comprise SEQ ID NO: 4 and SEQ ID NO: 5. Additional nucleic acid sequences useful for the detection of SEQ ID NO: 1+ bacteria and primers for sequencing and/or amplification thereof are presented in FIG. 11 and Table 2.

In an aspect of the method, the *Prevotella*-related species of bacteria comprising SEQ ID NO: 1, SEQ ID NO: 2, or SEQ ID NO: 3 is *P. copri* or is related to *P. copri*.

In a further aspect of the method, the amount of the *Prevotella*-related species of bacteria comprising SEQ ID NO: 1, SEQ ID NO: 2, or SEQ ID NO: 3 is determined using a reagent that specifically binds to the *Prevotella*-related species of bacteria or a nucleic acid sequence thereof. As envisioned herein, the reagent may be an antibody, an antibody derivative, an antibody fragment, a nucleic acid probe, an oligonucleotide, or an oligonucleotide primer pair specific for the *Prevotella*-related species of bacteria comprising SEQ ID NO: 1, SEQ ID NO: 2, or SEQ ID NO: 3. In a particular embodiment, the reagent is an oligonucleotide primer pair of SEQ ID NO: 4 and SEQ ID NO: 5 or is an oligonucleotide primer pair as set forth in Table 2 or FIG. 11. In another embodiment, the reagent is a nucleic acid probe as set forth in FIG. 11.

In an embodiment thereof, the determining of the amount of the *Prevotella*-related species of bacteria comprising SEQ ID NO: 1, SEQ ID NO: 2, or SEQ ID NO: 3 includes at least one assay selected from the group consisting of nucleic acid sequencing, PCR amplification, a competitive binding assay, a non-competitive binding assay, a radioimmunoassay, immunohistochemistry, an enzyme-linked immunosorbent assay (ELISA), a sandwich assay, a gel diffusion immunodiffusion assay, an agglutination assay, dot blotting, a fluorescent immunoassay such as fluorescence-activated cell sorting (FACS), a chemiluminescence immunoassay, an immunoPCR immunoassay, a protein A or protein G immunoassay, and an immunoelectrophoresis assay. In a more particular embodiment, the assay is nucleic acid sequencing or PCR amplication.

Also encompassed herein is a method for evaluating therapeutic efficacy of an agent administered to a patient with RA, the method comprising: measuring the amount of *Prevotella*-related species of bacteria comprising SEQ ID NO: 1, SEQ ID NO: 2, or SEQ ID NO: 3 before administration of the agent; measuring the amount of *Prevotella*-related species of bacteria comprising SEQ ID NO: 1, SEQ ID NO: 2, or SEQ ID NO: 3 after administration of the agent; and comparing the amount of the *Prevotella*-related species of bacteria comprising SEQ ID NO: 1, SEQ ID NO: 2, or SEQ ID NO: 3 determined before and after administration of the agent, wherein a decrease in the amount of the *Prevotella*-related species of bacteria comprising SEQ ID NO: 1, SEQ ID NO: 2, or SEQ ID NO: 3 after administration of the agent is a positive indicator of the therapeutic efficacy of the agent for RA. In a particular embodiment thereof, the method further comprises assessment of clinical symptoms of RA, ACPA/RF levels, or Th17/Treg levels in the patient with RA.

Also encompassed herein is a method for identifying a test substance that modulates levels of *Prevotella*-related species of bacteria comprising SEQ ID NO: 1, SEQ ID NO: 2, or SEQ ID NO: 3 in a subject, said method comprising a) determining the amount of the *Prevotella*-related species of bacteria comprising SEQ ID NO: 1, SEQ ID NO: 2, or SEQ ID NO: 3 in the biological sample obtained from said subject; b) contacting the biological sample with a test substance; and c) determining the amount of the *Prevotella*-related species of bacteria comprising SEQ ID NO: 1, SEQ ID NO: 2, or SEQ ID NO: 3 in the biological sample following contact with the test substance, wherein an alteration in the amount of the *Prevotella*-related species of bacteria determined in step c) relative to the amount determined in step a) identifies the test substance as a modulator of *Prevotella*-related species of bacteria comprising SEQ ID NO: 1, SEQ ID NO: 2, or SEQ ID NO: 3 levels.

In a particular embodiment thereof, a decrease in the amount of the *Prevotella*-related species of bacteria comprising SEQ ID NO: 1, SEQ ID NO: 2, or SEQ ID NO: 3 determined in step c) when compared to the amount of the Prevotella-related species of bacteria comprising SEQ ID NO: 1, SEQ ID NO: 2, or SEQ ID NO: 3 determined in step a) indicates that the test substance is a potential agent for treating or preventing RA in a subject.

Also encompassed herein is a composition for the prediction or diagnosis of new onset rheumatoid arthritis (RA) or the prognosis of a RA patient undergoing a therapeutic regimen, the composition comprising specific detection agents for determining the amount of the Prevotella-related species of bacteria comprising SEQ ID NO: 1, SEQ ID NO: 2, or SEQ ID NO: 3 and a buffer compatible with the activity of the specific detection reagents.

In a particular embodiment, the composition comprises specific detection reagents, including a nucleic acid probe, an oligonucleotide, or an oligonucleotide primer pair specific for the Prevotella-related species of bacteria comprising SEQ ID NO: 1, SEQ ID NO: 2, or SEQ ID NO: 3. In a particular embodiment, the specific detection reagent is a nucleic acid probe as set forth in FIG. 11. In another embodiment, the specific detection reagent is an oligonucleotide primer pair of SEQ ID NO: 4 and SEQ ID NO: 5 or is an oligonucleotide primer pair as set forth in Table 2 or FIG. 11. In yet another embodiment, the specific detection reagents comprise at least one sequence-specific oligonucleotide that binds specifically to 16S rRNA of the Prevotella-related species of bacteria comprising SEQ ID NO: 1, SEQ ID NO: 2, or SEQ ID NO: 3. The specific detection reagents may be labeled with a detectable moiety or moieties, linked to a moiety that confers immobilization properties, and/or immobilized on a solid phase support.

By "solid phase support or carrier" is intended any support capable of binding an oligonucleotide, antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art are aware of many other suitable carriers for binding oligonucleotide, antibody, or antigen, and are able to ascertain the same by use of routine experimentation.

Also encompassed herein is a method for inducing rheumatoid arthritis in a subject, the method comprising administering a dose of a Prevotella-related species of bacteria comprising SEQ ID NO: 1, SEQ ID NO: 2, or SEQ ID NO: 3 to the subject in an amount effective to induce rheumatoid arthritis in the subject. In a particular embodiment thereof, induction of rheumatoid arthritis is determined by assessing clinical symptoms of rheumatoid arthritis, ACPA/RF levels, and/or Th17/Treg levels in the subject.

In a further aspect, a method for inducing inflammatory arthritis or autoimmune disease in a subject is presented, the method comprising administering a dose of a Prevotella-related species of bacteria comprising SEQ ID NO: 1, SEQ ID NO: 2, or SEQ ID NO: 3 to the subject in an amount effective to induce inflammatory arthritis or autoimmune disease.

As described herein, the method for inducing rheumatoid arthritis in a subject or for inducing inflammatory arthritis or autoimmune disease in a subject may conducted in an embodiment wherein the subject is a mouse. More particularly, the mouse is a member of a mouse strain that is an animal model of human disease.

Other objects and advantages will become apparent to those skilled in the art from a review of the following description which proceeds with reference to the following illustrative drawings.

BRIEF DESCRIPTION OF THE DRAWINGS

FIG. 2 illustrates that the intestinal Prevotella genus is highly prevalent and abundant in new onset RA patients.

FIG. 3A shows a principal component analyses (PCA) of intestinal microbiome by groups. Most NORA patients (blue) cluster together and away from controls. Clustering is due to the overrepresentation of SEQ ID NO: 1+ bacteria. FIG. 3B shows that SEQ ID NO: 1+ bacteria is overrepresented in the intestinal microbiome of new-onset RA patients (NORA). CRA=chronic-RA. Significance vs. NORA= $P<0.01$; * $P<0.005$; ¶ $P<0.0005$; ¶¶ $P<0.000005$. FIG. 3C depicts a heat map showing high SEQ ID NO: 1+ bacterial abundance/prevalence in NORA.

FIG. 4A-C shows the nucleic acid sequences of SEQ ID NO: 1, SEQ ID NO: 2, and SEQ ID NO: 3. SEQ ID NO: 1 is the partial 16S sequence that distinguishes SEQ ID NO: 1+ bacteria. SEQ ID NO: 2 and SEQ ID NO: 3 are variants of SEQ ID NO: 1 and thus, are distinguishing features of SEQ ID NO: 1+ bacteria.

FIG. 10 shows that Prevotella copri colonization enhances collagen induced arthritis. Arthritis was induced with collagen injection with or without prior gavage with P. copri. Arthritis incidence and score were measured at weekly intervals for 12 weeks. Animals gavaged with P. copri had a higher incidence of arthritis and significantly higher score when compared to mice gavaged with media.

FIG. 11 shows nucleic acid sequences corresponding to SEQ ID NO: 1+ bacteria and primer pairs for amplification of same.

DETAILED DESCRIPTION

RA is a chronic, autoimmune condition of unknown etiology that, left untreated, leads to joint inflammation and destruction, deformity and long term disability. For more than a century, an infectious trigger for RA has been sought. Most studies have relied upon indirect serological evidence. The use of culture-independent, massively parallel DNA sequencing technology now allows for identification of most bacterial species. There are about 1100 bacterial species described in the human intestinal tract.

The human body comprises up to 100 trillion microbial cells that encode 100-fold more unique genes than those encoded by the 10 trillion human cells therein. High-throughput sequencing has revealed that correlations exist between the microbiome (total microbes of the body) and human health. *Porphyromonas gingivalis* of the oral cavity, for example, has been associated with RA. Gut microbiota has also been associated with autoimmune disease in animal models via Th17 cell activation. Examples of such a linked relationship include: experimental colitis and autoimmune encephalitis. The role of intestinal commensal microbiota in mice with RA-like disease has, furthermore, been established. More particularly, Ivanov et al. (2009; Cell 139:485-498) demonstrated that the commensal intestinal bacteria segmented filamentous bacteria (SFB) is sufficient to induce Th17 differentiation mice. Wu et al. (2010; Immunity 32:815-827) demonstrated that in an animal model for autoimmune arthritis (K/BxN), SFB drives K/BxN arthritis via Th17 cells. In contrast, control K/BxN mice maintained in germ-free conditions do not develop arthritis. Wu et al. further demonstrated that treatment with vancomycin to reduce bacterial load, decreases Th17 cells in K/BxN mice and thus, prevents joint inflammation.

To explore the potential causes of RA in humans, the present inventors set out to investigate if human intestinal and/or oral microbiota differ in RA patients versus normal individuals and do differences in microbiota alter the Th17/T regulatory (Treg) cell balance. As described herein, the present inventors used clinical parameters: RA disease activity as measured by DAS28 and MD-HAQ; dental assessment: periodontal status as evaluated by probing depth, attachment loss, and bleeding on probing; immunologic studies: rheumatoid factor (RF) and anti-citrullinated protein antibody (ACPA) titers, circulating Th17 cells (using fluorescence activated cell sorting; FACS), and Treg functional assays; and microbiome (oral and intestinal) analysis: 16s rRNA high-throughput pyrosequencing (454 Titanium) as methods in cross-sectional and prospective analyses of RA patients.

Results pertaining to the cross-sectional study performed reveal that clinical periodontal disease prevalence is higher in patients with RA. The present inventors have, moreover, demonstrated that the abundance of a particular species of bacteria, *Porphyromonas gingivalis* is higher in RA patients.

Figure 1:
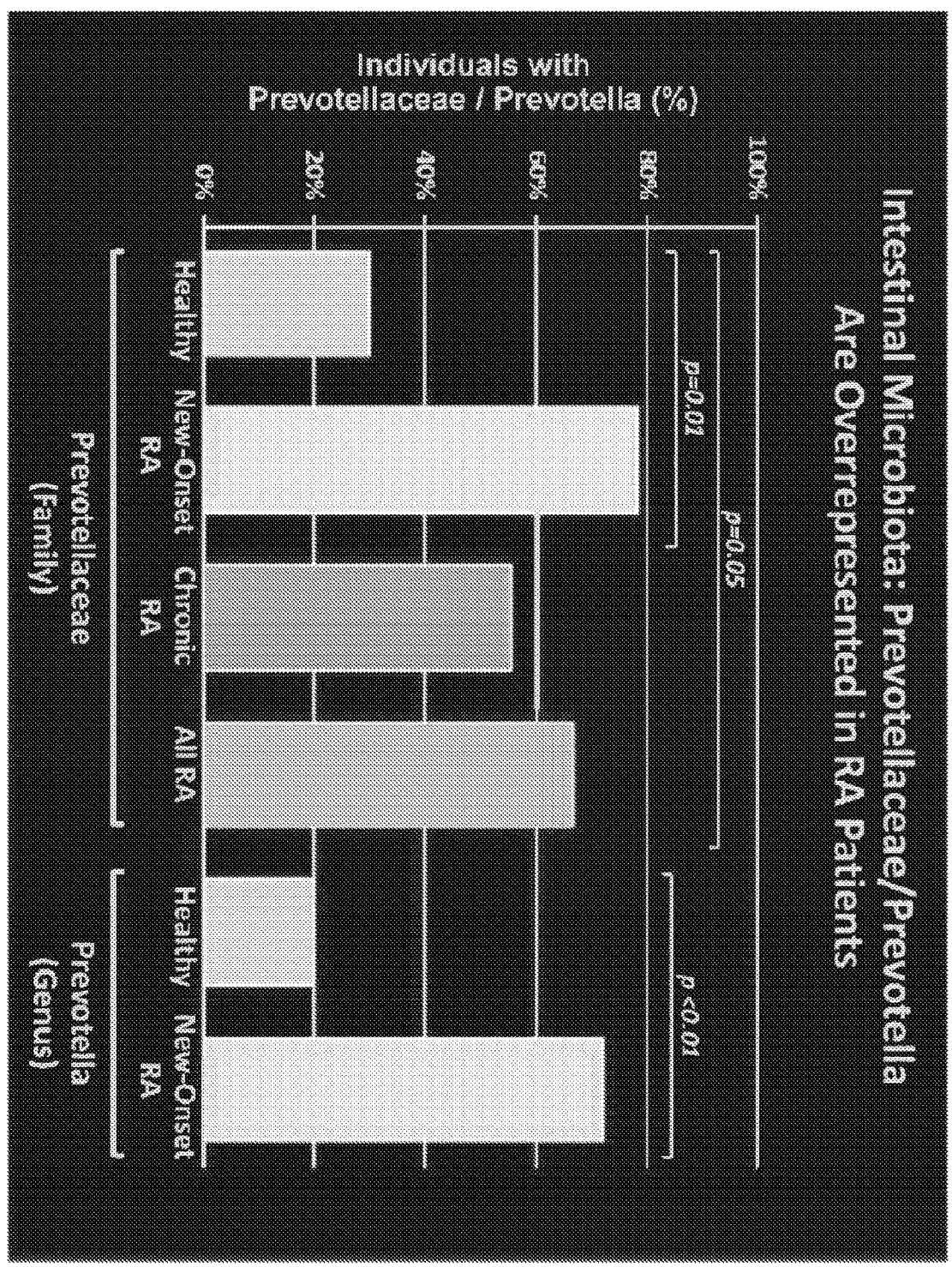
FIG. 1 shows a histogram bar graph showing that Prevotellaceae/Prevotella are over-represented in the intestinal microbiota of RA patients.

With respect to intestinal microbiota, results presented herein show that the Prevotellaceae family and the *Prevotella* species are over-represented in RA patients. See, for example, FIG. 1. As shown therein, the Y axis shows the percentage of subjects who carry these gut bacteria and each column describes the indicated different group. Intriguingly, the differences are significantly more pronounced in new onset RA (NORA) patients when compared to established RA disease.

Also presented herein are results showing that the intestinal *Prevotella* genus as a whole is highly prevalent and abundant in NORA patients. See, for example, FIG. 2. Indeed, the *Prevotella* genus is even more significantly overrepresented in NORA patients. A relative abundance scale of the heat map analysis is shown in FIG. 2 at the left side. High *Prevotella* abundance is defined as greater than 20% of total microbiota. As seen in the top panel, about 75% of NORA patients have an overabundance of gut *prevotella* as compared to 20% of healthy controls. In contrast, the Human Microbiome Project consortium described intestinal *Prevotellas* in only 30% of healthy subjects, most at ~1% abundance.

The *Prevotella* genus falls within the Bacteroidetes phylum and comprises gram-negative, commensal anaerobes. The genus *Prevotella* is found throughout the human body and is represented, for example, in the human oral, intestinal and urogenital flora. The genus has been implicated in various infections of the head and neck, lower respiratory tract, central nervous system, abdominal and female genital tract and in bacteraemia (Jousimies-Somer et al. 2002; Wadsworth—KTL Anaerobic Bacteriology Manual, 6th ed. Belmont, Calif.: Star Publishing). According to Alauzet et al. (Future Microbiology 2010, 5:1695-1718; the entire contents of which is incorporated herein in its entirety), there are 45 currently recognized bacterial species in the genus *Prevotella* and several taxonomically controversial species. Alauzet et al., moreover, indicate that the diversity of the genus is far from fully known. Intestinal *Prevotellas* express characteristic enzymes, including those of the PAD-like superfamily, DHF reductase, and AICAR transformylase.

The significance of the expression of peptidylarginine deiminase (PAD)-like enzymes relates to the ability of these enzymes to deiminate arginine. Deimination (citrullination) of arginine side chains to form peptidylcitrulline is one of many recognized post-translational modifications of this amino acid. This post-translational conversion is catalyzed by the family of PAD enzymes, of which humans express five (PAD1 to 4 and PAD6) isoforms. The process of protein citrullination plays a vital role in normal physiology, in which it is involved in the formation of rigid structures such as hair, skin, and myelin sheaths (Wegner et al. 2009; Immunol Rev 233:1-21).

Arginine is a positively charged, hydrophilic amino acid that is often found on the surface of proteins, where it participates in ionic interactions with other amino acid side chains and forms stabilizing hydrogen bonds with both the peptide backbone and amino acid side chains. These properties confer upon arginine a significant role in the three-dimensional organization of proteins and their interaction with other biological molecules. Accordingly, posttranslational modification of arginine can alter three dimensional protein structure and function and potentially expose previously hidden epitopes to the immune system.

Aberrant citrullination has, in fact, been observed in diseases of the skin and nervous system and in inflammatory arthritides, of which RA is one example (Wegner et al. 2009; Immunol Rev 233:1-21). Despite the ubiquity of citrullinated proteins, the autoantibody response to citrullinated proteins is largely restricted to RA (Schellekens et al. 2000; Arthritis Rheum 43:155-163). The switch that leads to the generation of antibodies to citrullinated peptides and thus loss of immune tolerance to citrullinated proteins is likely to involve a complex interplay of individual genetic and environmental factors.

Figure 3A:
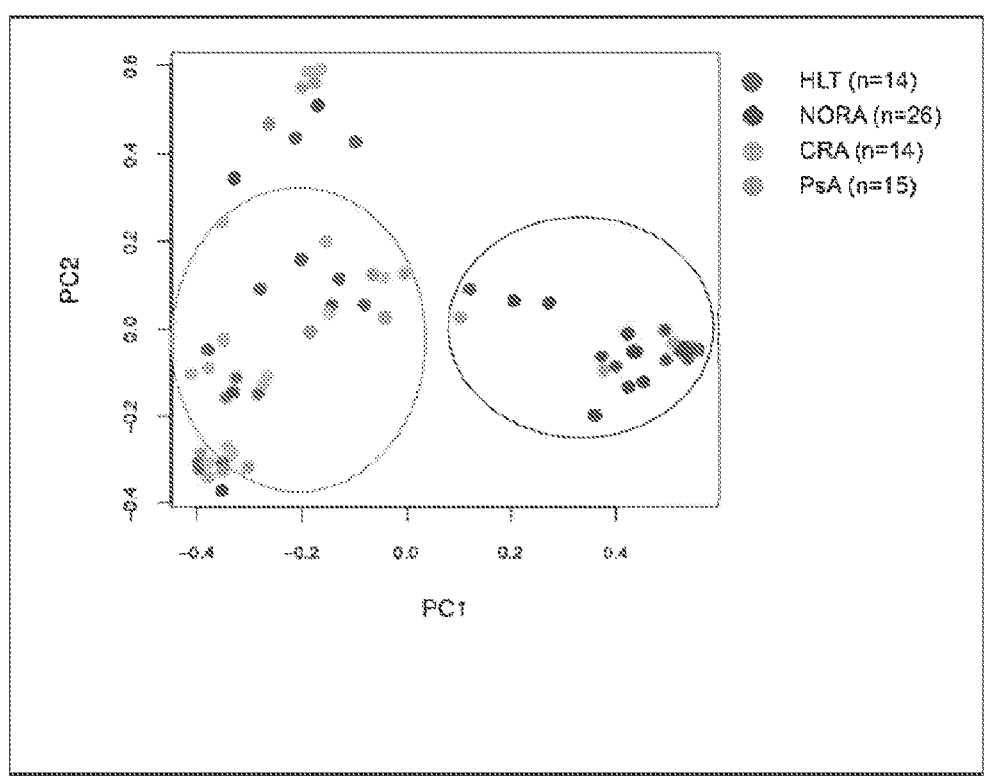
FIG. 3A-C shows that a particular bacterial species comprising SEQ ID NO: 1 (SEQ ID NO: 1+ bacteria), which is an intestinal Prevotella species or a Prevotella related species, is present at significantly higher prevalence and abundance in the gut microbiome of ACPA+ NORA patients compared to healthy individuals and chronic-treated RA patients.
Figure 3B:
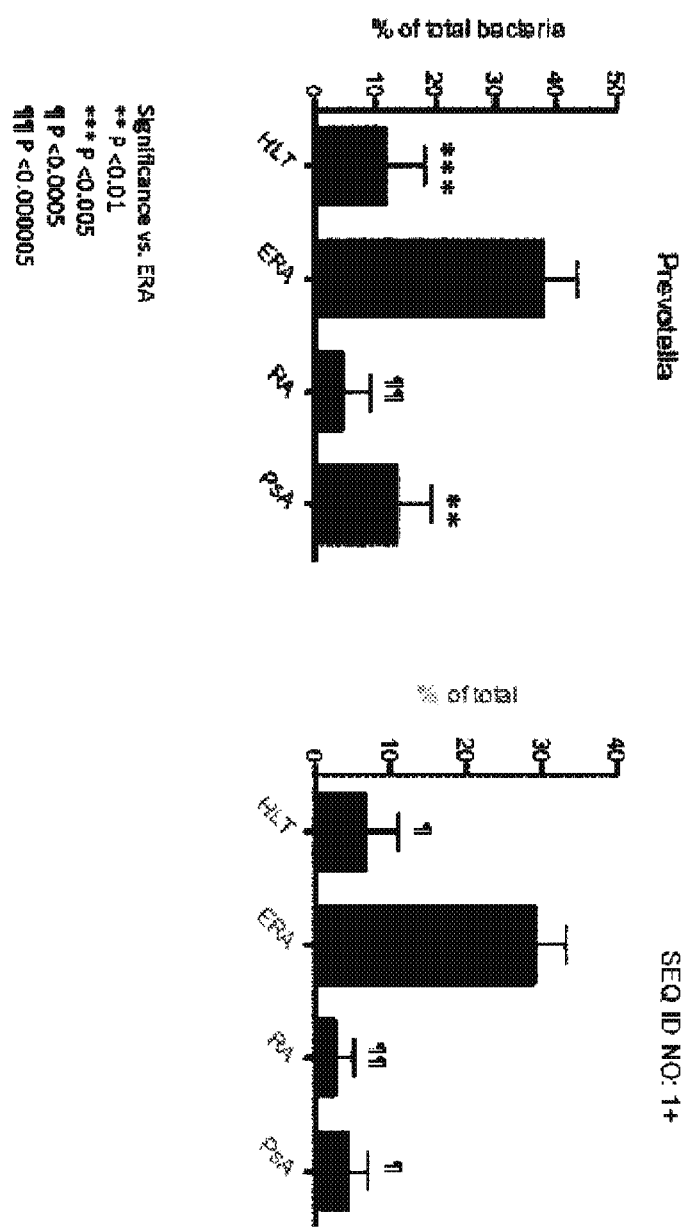
Figure 3C:
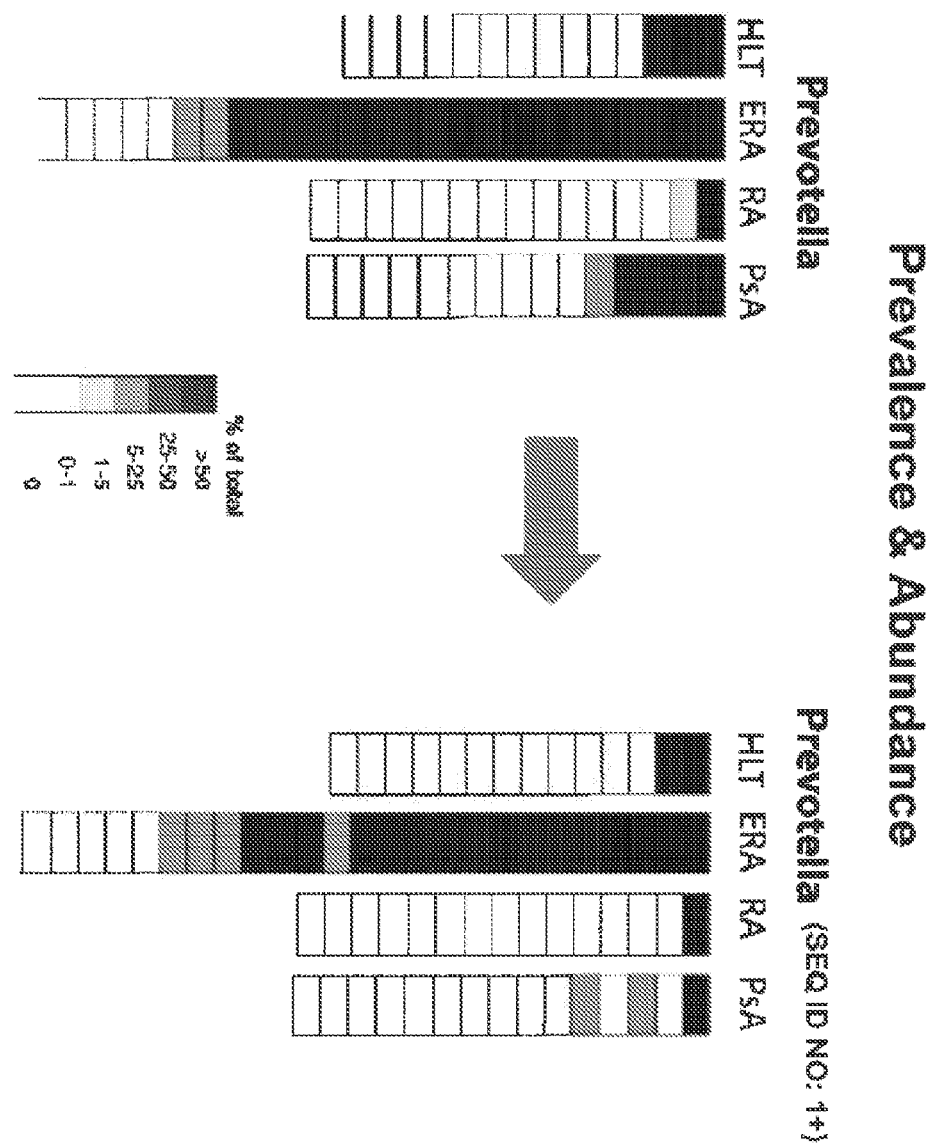

As described herein, the present inventors have discovered that a particular bacterial species comprising SEQ ID NO: 1 (SEQ ID NO: 1+ bacteria) of intestinal origin appears to be associated with and causative of RA in human subjects. SEQ ID NO: 1+ bacteria appears to be a *Prevotella* or *Prevotella* related species of bacteria. More particularly, the SEQ ID NO: 1+ bacteria appears to be *P. copri* or a species related thereto. Further to the above and as shown in FIG. 3A-C, the present inventors have made the novel discovery that the SEQ ID NO: 1+ bacteria is present at significantly higher prevalence and abundance in the gut microbiome of ACPA+ NORA patients compared to healthy individuals and chronic-treated RA patients. The present inventors also demonstrate herein that DMARD naive NORA patients exhibit a distinct intestinal microbiome, characterized by an unexpectedly high abundance of SEQ ID NO: 1+ bacteria. Accordingly, the presence and abundance of the SEQ ID NO: 1+ bacterial species in a human subject, particularly in the intestinal tract, can be used as a diagnostic indicator for RA onset.

The identification of a biomarker for early disease that serves as a simple genetic marker that can be assayed using a stool sample provides a useful tool for identifying patients at-risk for RA development and in the early phases of disease, so therapy can be instituted and tissue damage, deformity and disability can potentially be prevented. The biomarkers described herein, SEQ ID NO: 1+, SEQ ID NO: 2+, and SEQ ID NO: 3+ nucleic acid sequences, detection of which serves as an indicator of SEQ ID NO: 1+ bacterial species, can be used alone or in combination with others biomarkers for RA or new-onset RA. The nucleic acid sequence corresponding to SEQ ID NO: 1, SEQ ID NO: 2, and SEQ ID NO: 3 are presented in FIG. 4.

Figure 5:
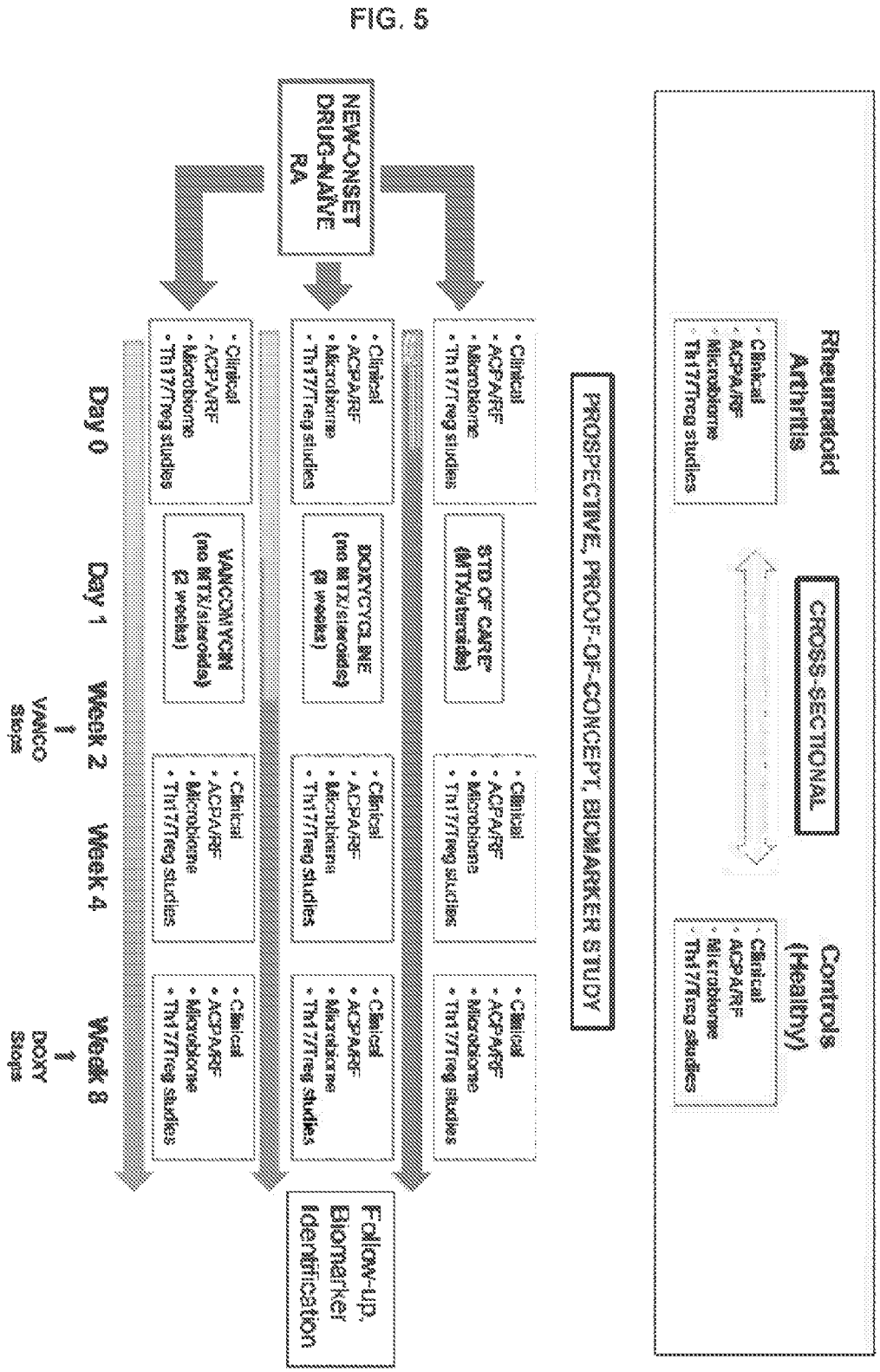
FIG. 5 shows a flow chart of a prospective, proof-of-concept biomarker study.

The identification of a biomarker for RA, namely detection of the presence of SEQ ID NO: 1+ bacteria, also provides a tool with which the efficacy of a therapeutic regimen can be evaluated in an ongoing basis. Further to this end, the present inventors have designed a prospective, proof-of-concept, biomarker study which is depicted in FIG. 5. In accordance with the protocol set forth in FIG. 5, only NORA disease-modifying anti-rheumatic drug negative (DMARD−) naive RA patients are enrolled and assigned to either standard of care therapy [i.e., background methotrexate (MTX)/low dose steroids] or short courses of antibiotics: doxycycline (in view of its known activity against *porphyromonas*) or vancomycin (in light of findings presented herein). The same parameters indicated therein with respect to baseline are analyzed at weeks 4 and 8. Comparison of these parameters at different stages during the time course of the study accurately reflects patient response to the therapeutic regimen with which they are being treated.

In accordance with the results presented herein, a determination of the relative levels of SEQ ID NO: 1+ bacteria (e.g., at onset and after various treatment duration times) is envisioned as a parameter for inclusion in the study presented in FIG. 5. Accordingly, the parameter of microbiome analysis is to be performed in general and particularly with respect to levels of SEQ ID NO: 1+ bacteria. An assessment of whether or not a treatment regimen reduces the level of SEQ ID NO: 1+ bacteria will inform a skilled practitioner as to whether or not the regimen is efficacious for RA. In a particular embodiment, therefore, the therapeutic efficacy of a treatment regimen is reflected positively by a decrease in SEQ ID NO: 1+ bacterial levels.

Figure 6:
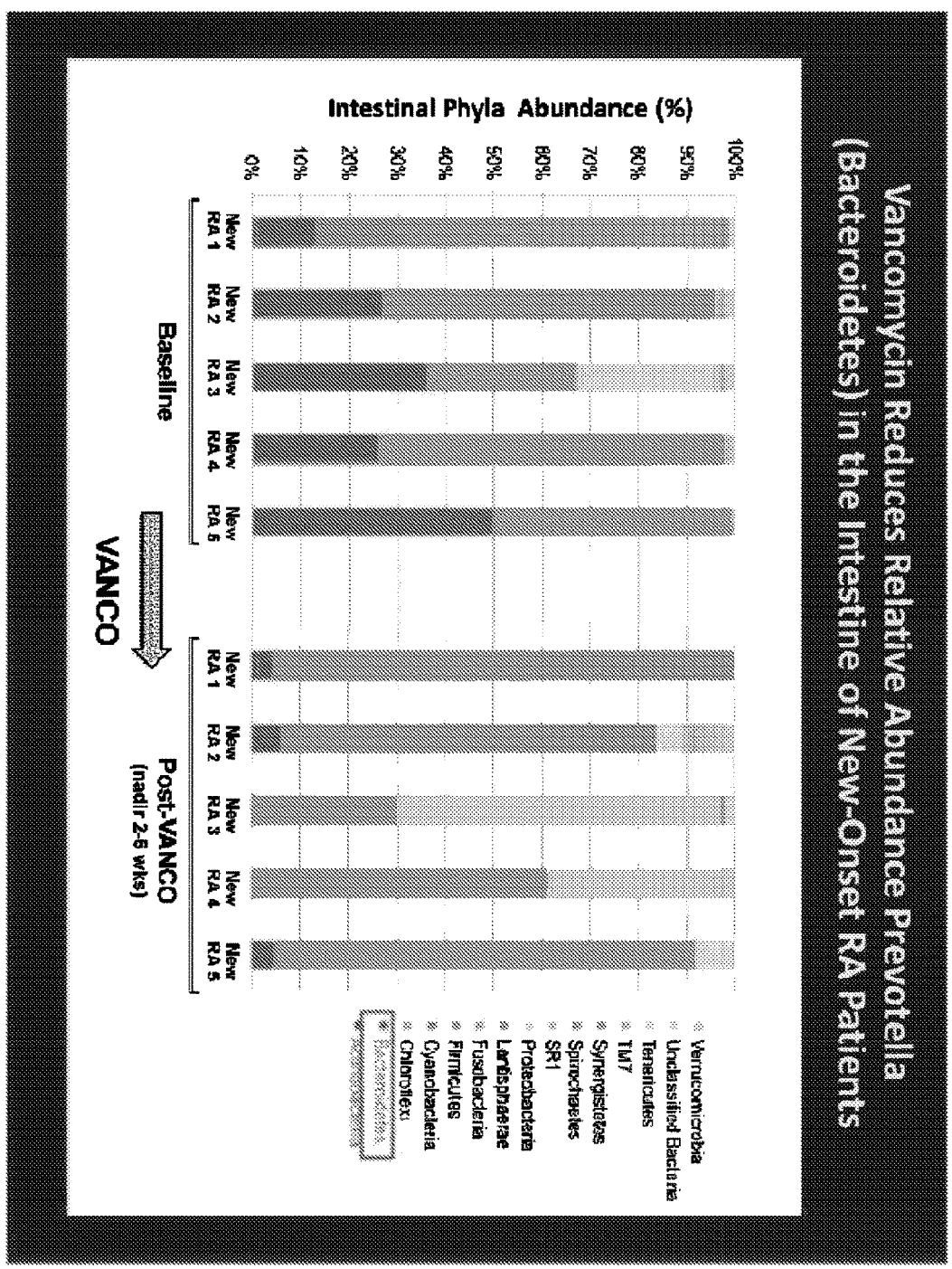
FIG. 6 shows a graph depicting the efficacy of vancomycin with respect to reducing the relative abundance of Prevotella (Bacteroidetes) in the intestine of new-onset RA patients.
Figure 7:
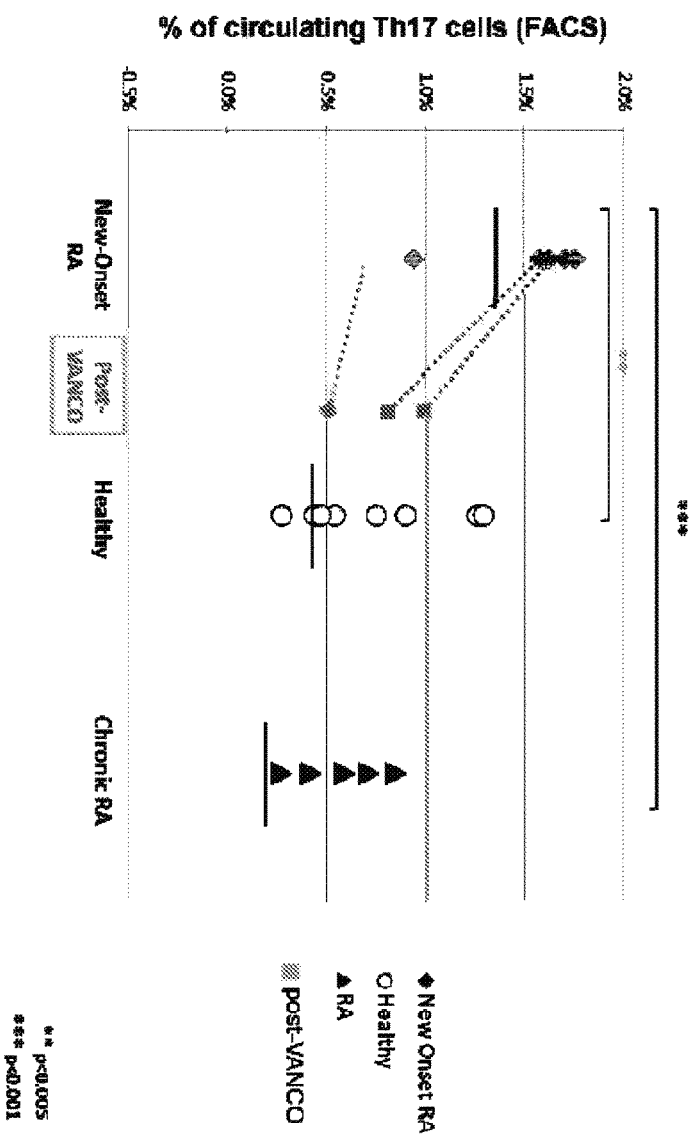
FIG. 7 depicts a graph showing that circulating Th17 cells are increased in new-onset RA patients and the number of circulating Th17 cells decreases following vancomycin treatment.

FIG. 6 shows that vancomycin reduces relative abundance of *Prevotella* (Bacteroidetes) in the intestine of NORA patients. The graph shown in FIG. 6 illustrates the baseline intestinal phyla in new onset RA patients, each bar representing a single patient. In red, is the relative abundance of *Prevotellas*/Bacteroidetes. Other colors reflect the rest of the phyla diversity. Following vancomycin treatment, there is a decrease in intestinal Bacteroidetes/*Prevotella* in NORA patients within 6 weeks after cessation of therapy. The decrease can, in fact, be quite dramatic, Moreover, as shown in FIG. 7, circulating Th17 cells are increased in NORA patients and the number of circulating Th17 cells decreases following vancomycin treatment. As determined by fluorescence activated cell sorting (FACS), there is a two-fold increase in total Th17 cells when compared to controls. Post vancomycin treatment, however, there is a decline in the number of these cells, suggesting that Th17 cells and/or levels respond to alterations in gut microbiota.

Figure 8:
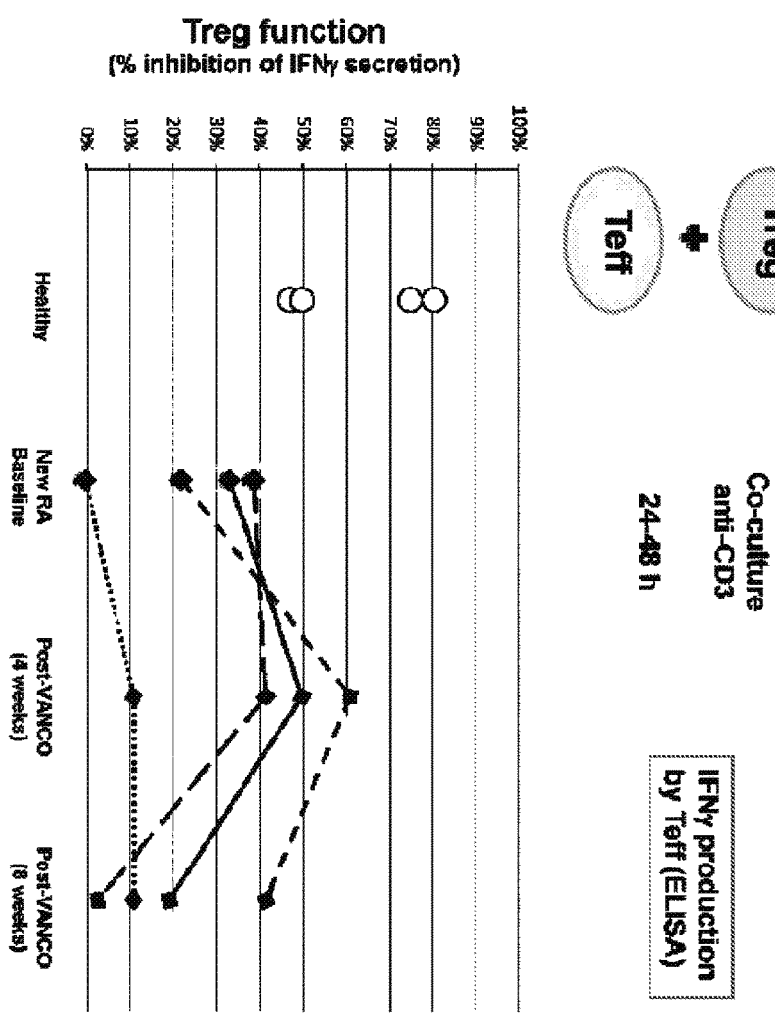
FIG. 8 presents a graph revealing that vancomycin treatment also leads to transient recovery of Treg function.

As shown in FIG. 8, vancomycin treatment also leads to transient recovery of Treg function. In brief, functional assays can be performed using rheumatoid regulatory T cells (Tregs) co-cultured with autologous effector T cells. As a readout of Treg activity in such assays, supernatants from these co-cultures are harvested and analyzed for the presence of IFN-γ after 24-48 hours. In healthy individuals, Tregs are able to inhibit effector T cell production of IFN gamma. For the sake of clarity with regard to FIG. 8, a higher percentage as reflected in the Y axis indicates better Treg function. In contrast, NORA Tregs have decreased inhibitory function. The use of vancomycin, therefore, is not only associated with a decrease in the abundance of *Prevotellas* and *Prevotella*-related species (such as SEQ ID NO: 1+ bacteria), but also with a transient recovery of Treg function at 4 weeks, which declines at a later time point. These findings suggest regulatory T cells from some NORA patients partially and transiently recover their pro-tolerogenic function within 2 months of vancomycin treatment.

Figure 9:
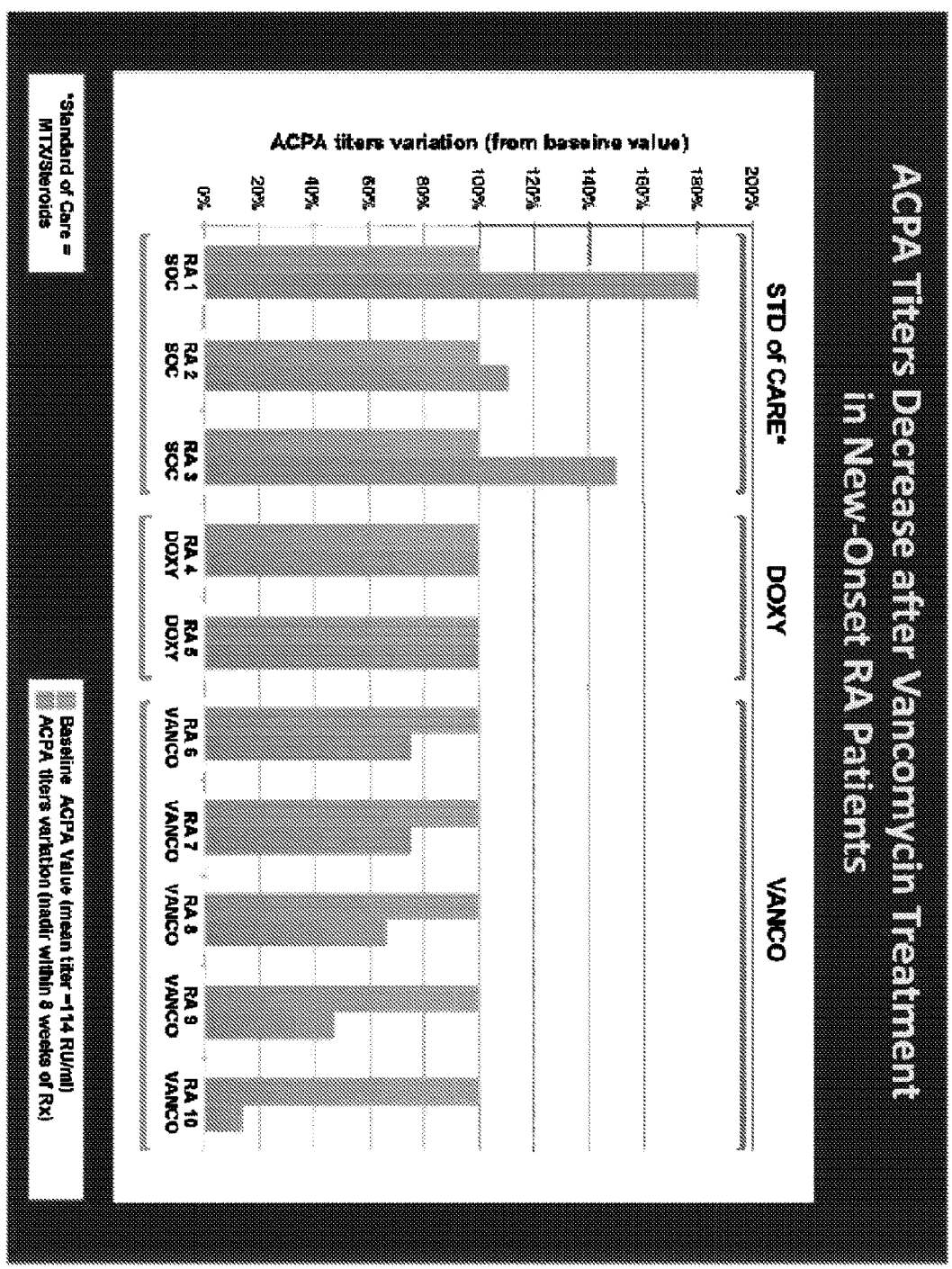
FIG. 9 shows a histogram bar graph showing that anti-citrullinated protein antibody (ACPA) titers are also significantly decreased after vancomycin treatment in new-onset patients.

Further to the above, ACPA titers are also significantly decreased after vancomycin treatment in NORA patients. See FIG. 9. By way of explanation, the Y axis is the ACPA titer variation from baseline values (in blue bars) therein. As shown in FIG. 9, there is actually an increase in ACPA titers in the standard of care (SOC) patient group after treatment and no change in ACPA titers in patients treated with doxycycline. This stands in dramatic contrast to the marked decrease in ACPA titers observed in patients within 2 months of initiation of vancomycin therapy. In light of the above, it is apparent that the relative abundance of *Prevotella* (*Bacteroides*) in the intestine of NORA patients can be viewed as a biomarker of NORA and treatment with vancomycin satisfies the criteria of a therapeutic agent for treatment of same.

More particularly, as described herein, the relative abundance of SEQ ID NO: 1+ bacteria in the intestine of NORA patients is a biomarker of NORA and can thus be used as a diagnostic indicator of NORA or predisposition to NORA and as a prognostic indicator that reflects efficacy of a therapeutic regimen in an ongoing manner.

It is, furthermore, expected that the novel biomarkers described herein, SEQ ID NO: 1, SEQ ID NO: 2, and SEQ ID NO: 3 nucleic acid sequences, detection of any of which serves as an indicator of SEQ ID NO: 1+ bacterial species will be validated in accordance with the proof-of-concept, biomarker study set forth in FIG. 5.

With regard to the results presented in FIG. 10, arthritis was induced by injecting collagen as described by Brand et al. (Nature Protocols 2: 1269-1275; 2007). In brief, six B6 mice were treated with antibiotic therapy for at least 48 hs. Three animals were gavaged with *Prevotella copri* and the other three only with media. Two weeks after gavage, complete Freund's adjuvant (CFA) was injected intradermally in the skin of the tail of all animals to induce arthritis. Arthritis incidence and score were measured at weekly intervals for 12 weeks. Animals gavaged with *P. copri* had a higher incidence of arthritis and significantly higher score when compared to mice gavaged with media alone. See FIG. 10.

Additional sequences and primer pairs suitable for polymerase chain reaction (PCR) mediated amplification thereof are presented in FIG. 11. The nucleic acid sequences shown therein are thought to distinguish SEQ ID NO: 1+ bacteria and thus provide probes and primers for detection thereof. Briefly, these nucleic acid sequences were identified via a multifaceted analysis of differential open reading frame expression patterns. The nucleic acid sequences are listed by cluster number. Notably, cluster 04539 is referred to herein as "RhuM" because it has a short protein domain which by Pfam maps to a virulence RhuM domain. The protein domain itself is not unique, but the sequence of cluster 04539 appears to be unique to the *P. copri*-NORA genome (SEQ ID NO: 1+ bacteria). Cluster 04813 comprises a vWFA2 domain. This does exhibit homology (max identity 92%) to the reference genome, but comprises nucleotide changes that distinguish it from that of the reference genome and it was identified as differentially regulated. Primer sequences are also listed below the nucleic acid sequences presented in FIG. 11. The present inventors have verified the ability of the primers for cluster 04539 to amplify sequences from *P. copri*-NORA (SEQ ID NO: 1+) but not reference genome. Additional results have verified many of the other primer sequences listed therein.

In summary, an increased prevalence of periodontal disease is observed in RA patients and high relative abundance of *Porphyromonas gingivalis*, as determined by 16s rRNA sequencing, is noted in the subgingival plaque of RA patients. A high prevalence of *Prevotella* species is detected in the intestine of RA patients, particularly new-onset RA patients. Results presented herein also demonstrate that in patients with new-onset, DMARD-naive, ACPA+ RA, the Th17/Treg balance is skewed from normal. In short, an increase in the total number of circulating Th17 cells is observed in such patients, as is a decrease in Treg function. Vancomycin treatment of new-onset, DMARD-naive, ACPA+ RA patients results in a decrease in the number of *Prevotella* in the gut within 8 weeks post-treatment, a decrease in the number of peripheral (circulating) Th17 cells, a reversal of Treg dysfunction, and a decrease in ACPA titers.

Further to the above, the present inventors have identified novel biomarkers for NORA, namely the detection of SEQ ID NO: 1+ bacteria in the intestinal microflora of subjects having NORA or having susceptibility to acquiring same.

In accordance with the findings presented herein, alteration of oral and/or gut microbiota leads to auto-inflammatory responses in new-onset RA patients. Mechanisms through which this succession of events manifests include the generation of cyclic citrullinated peptides and/or a shift in Th17/Treg balance. The present inventors have, moreover, identified SEQ ID NO: 1+ bacteria in the intestinal microflora as a trigger for and/or an associative factor in the development of such auto-inflammatory responses in new-onset RA patients.

There is a need for improved methods for determining RA risk, particularly in those patients with a familial history of RA. There is, moreover, a need for diagnostic tools with which skilled practitioners can monitor asymptomatic, high risk patients using minimally invasive techniques to assess, on an ongoing basis, risk of RA onset. Improved diagnostic tools with which skilled practitioners can determine how best to treat a patient diagnosed with RA are also sought. These tools can, furthermore, be applied to methods for assessing if a therapeutic regimen is efficacious for the patient. The discoveries described herein address the above-indicated long sought diagnostic, prognostic, and therapeutic needs.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

TABLE 1

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

Two amino acid sequences are "substantially homologous" when at least about 70% of the amino acid residues (preferably at least about 80%, and most preferably at least about 90 or 95%) are identical, or represent conservative substitutions.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The subject or patient is preferably an animal, including but not limited to animals such as mice, rats, cows, pigs, horses, chickens, cats, dogs, etc., and is preferably a mammal, more preferably a primate, and most preferably a human.

The term "preventing" or "prevention" refers to a reduction in risk of acquiring or developing a disease or disorder (i.e., causing at least one of the clinical symptoms of the disease not to develop in a subject that may be exposed to a disease-causing agent, or predisposed to the disease in advance of disease onset).

The term "prophylaxis" is related to "prevention" and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

The term "treating" or "treatment" of any disease or disorder refers, in one embodiment, to ameliorating the disease or disorder (i.e., arresting the disease or reducing the manifestation, extent or severity of at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

As used herein, the term new-onset rheumatoid arthritis (NORA) patient refers to any patient who fulfills 1987 ARA criteria and/or 2010 ACR/EULAR criteria for Rheumatoid Arthritis. Patients must have been recently diagnosed (less than six months of symptoms) and never treated with steroids or DMARDs. The exclusion criteria are, moreover, set forth in Example 1 below.

As used herein, the term "immune response" signifies any reaction produced by an antigen, such as a protein antigen, in a host having a functioning immune system. Immune responses may be either humoral, involving production of immunoglobulins or antibodies, or cellular, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems.

An "immunological response" to a composition or vaccine comprised of an antigen is the development in the host of a cellular- and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to preferably reduce by at least about 30 percent, more preferably by at least 50 percent, most preferably by at least 90 percent, a clinically significant change in a pathological feature of a disease or condition.

The compositions containing the molecules or compounds of the invention can be administered for diagnostic and/or therapeutic treatments. In therapeutic applications, compositions are administered to a patient already suffering from RA, for example, in an amount sufficient to at least partially arrest the symptoms of the disease and its complications. An amount adequate to accomplish this is defined as a "therapeutically effective amount or dose." Amounts effective for this use will depend on the severity of the disease and the weight and general state of the patient.

Compounds, such as antibiotics (e.g., vancomycin), for use in the invention may be prepared in pharmaceutical compositions, with a suitable carrier and at a strength effective for administration by various means to a patient experiencing an adverse medical condition associated with early-onset RA, wherein increased numbers of SEQ ID NO: 1+ bacteria are detected, for the treatment thereof. A variety of administrative techniques may be utilized, among them parenteral techniques such as subcutaneous, intravenous and intraperitoneal injections, catheterizations and the like. Average quantities of the compounds or derivatives thereof may vary and in particular should be based upon the recommendations and prescription of a qualified physician or veterinarian.

Also, antibodies including both polyclonal and monoclonal antibodies, and other drugs that modulate the proliferation or activity of SEQ ID NO: 1+ bacteria may possess certain diagnostic and/or therapeutic applications. For example, SEQ ID NO: 1+ bacteria or components thereof, such as cell wall components, may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of SEQ ID NO: 1+ bacteria or components thereof may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against SEQ ID NO: 1+ bacteria or components thereof can be screened for various properties; i.e., isotype, epitope, affinity, etc. Such monoclonals can be readily identified in activity assays. High affinity antibodies are also useful for immunoaffinity purification purposes.

Preferably, an antibody produced against SEQ ID NO: 1+ bacteria or components thereof used in the diagnostic methods of this invention is an affinity purified polyclonal antibody. More preferably, the antibody is a monoclonal antibody (mAb). In addition, it is preferable for the antibody produced against SEQ ID NO: 1+ bacteria or components thereof used herein to be in the form of Fab, Fab', F(ab')$_2$ or F(v) portions of whole antibody molecules.

Methods for producing polyclonal anti-polypeptide antibodies are well-known in the art. See U.S. Pat. No. 4,493,795 to Nestor et al. A monoclonal antibody, typically containing Fab and/or F(ab')$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

Methods for producing monoclonal antibodies are also well-known in the art. See Niman et al., *Proc. Natl. Acad. Sci. USA*, 80:4949-4953 (1983). Typically, the SEQ ID NO: 1+ bacteria component (e.g., a cell wall component) is used either alone or conjugated to an immunogenic carrier, as the immunogen as described above. The hybridomas are screened for the ability to produce an antibody that immunoreacts with the particular immunogen used.

The present invention further contemplates therapeutic compositions useful in practicing the therapeutic methods of this invention. A subject therapeutic composition includes, in admixture, a pharmaceutically acceptable excipient (carrier) and one or more of an agent (e.g., an antibiotic or the like) that inhibits the proliferation and/or activity of a SEQ ID NO: 1+ bacteria or component thereof, as described herein as an active ingredient.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or cell modulation desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

A general method for site-specific incorporation of unnatural amino acids into proteins is described in Christopher J. Noren, Spencer J. Anthony-Cahill, Michael C. Griffith, Peter G. Schultz, *Science*, 244:182-188 (April 1989). This method may be used to create analogs with unnatural amino acids.

With respect to antibodies or binding partners or functional fragments thereof, the immunogen (e.g., a SEQ ID NO: 1+ bacterial component) forms complexes with one or more antibody(ies) or binding partners and one member of the complex is labeled with a detectable label. The fact that a complex has formed and, if desired, the amount thereof, can be determined by known methods applicable to the detection of labels.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The antibodies or binding partners or functional fragments thereof specific for SEQ ID NO: 1+ bacteria or components thereof can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

As used herein, the term "complementary" refers to two DNA strands that exhibit substantial normal base pairing characteristics. Complementary DNA may, however, contain one or more mismatches.

The term "hybridization" refers to the hydrogen bonding that occurs between two complementary DNA strands.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it is generally associated in its natural state (i.e., in cells or tissues). An isolated nucleic acid (either DNA or RNA) may further represent a molecule produced directly by biological or synthetic means and separated from other components present during its production.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 60%, but often, more than 85%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

The terms "percent similarity", "percent identity" and "percent homology" when referring to a particular sequence are used as set forth in the University of Wisconsin GCG software program and are known in the art.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the basic and novel characteristics of the sequence.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression vector" or "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the term "operably linked" refers to a regulatory sequence capable of mediating the expression of a coding sequence and which are placed in a DNA molecule (e.g., an expression vector) in an appropriate position relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "oligonucleotide," as used herein refers to primers and probes described herein, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield an primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Primers and/or probes may be labeled fluorescently with 6-carboxyfluorescein (6-FAM). Alternatively primers may be labeled with 4, 7, 2', 7'-Tetrachloro-6-carboxyfluorescein (TET). Other alternative DNA labeling methods are known in the art and are contemplated to be within the scope of the invention.

In a particular embodiment, oligonucleotides according to the present invention that hybridize to nucleic acid sequences identified as specific to the SEQ ID NO: 1+ bacteria described herein, are at least about 10 nucleotides in length, more preferably at least 15 nucleotides in length, more preferably at least about 20 nucleotides in length. Further to the above, fragments of nucleic acid sequences identified as specific to the SEQ ID NO: 1+ bacteria described herein represent aspects of the present invention. Such fragments and oligonucleotides specific for same may be used as primers or probes to determining the amount of a *Prevotella*-related species of bacteria in a biological sample obtained from a subject, wherein the *Prevotella*-related species of bacteria comprises SEQ ID NO: 1, SEQ ID NO: 2, or SEQ ID NO: 3. Primers such as those described herein (e.g., SEQ ID NOs: 4 and 5) may, moreover, be used in polymerase chain reaction (PCR) assays in methods directed to determining the amount of a *Prevotella*-related species of bacteria in a biological sample obtained from a subject, wherein the *Prevotella*-related species of bacteria comprises any one of SEQ ID NO: 1, 2, or 3.

TABLE 2

Primer pairs specific for SEQ ID NO: 1+ bacteria:

| Name | Primer sequence | TM |
| --- | --- | --- |
| 1F | CGCCCTCGTTGCCACTGGAG (SEQ ID NO: 6) | 63.4 |
| 1R | TTGAAATCCGGCAGGCGGCA (SEQ ID NO: 7) | 63.2 |

TABLE 2-continued

Primer pairs specific for SEQ ID NO: 1+ bacteria:

| Name | Primer sequence | TM |
|---|---|---|
| 2F | AGGGAGAACGACCTGCGCCT (SEQ ID NO: 8) | 63.6 |
| 2R | GGCACACGGGTTGAGCGGAA (SEQ ID NO: 9) | 63.1 |
| 3F | TCTGCCACCACGTCCTCGCT (SEQ ID NO: 10) | 63.7 |
| 3R | AGCCGACTAACCCAGGCGGT (SEQ ID NO: 11) | 63.7 |
| 4F | CCTACGATGGCGCACAGGGC (SEQ ID NO: 12) | 63.5 |
| 4R | TCGCCGAATACGCTGCTGGC (SEQ ID NO: 13) | 63.1 |
| 5F | TGCGATGCACITGCCACCGA (SEQ ID NO: 14) | 62.6 |
| 5R | GATGGCAGCCTTGTCGCGGT (SEQ ID NO: 15) | 63.2 |
| 6F | GTCGCCGGGGCGGTTTCTTT (SEQ ID NO: 16) | 63.4 |
| 6R | TGTTCGTTGCGCCCCTTGCT (SEQ ID NO: 17) | 62.9 |
| 7F | CCCACGATGGGCATCAGCCG (SEQ ID NO: 18) | 63.7 |
| 7R | GTCGCTTGCCAGGGCGTTCA (SEQ ID NO: 19) | 63.4 |
| 8F | CACCGCCTGGGTTAGTCGGC (SEQ ID NO: 20) | 63.2 |
| 8R | AGGTCAGGCGCTGCTTTGC (SEQ ID NO: 21) | 63.6 |
| 9F | AGCAACGCCACGAAGCTGGT (SEQ ID NO: 22) | 62.6 |
| 9R | TCAGCCAGGCGCCAATCACG (SEQ ID NO: 23) | 63.2 |
| 10F | TGCGCAGAAACGGCAAGGGA (SEQ ID NO: 24) | 62.6 |
| 10R | TGGCAGCCATGCTGTACGCC (SEQ ID NO: 25) | 63.3 |
| 11F | GTCCGCCCTCGTTGCCACTG (SEQ ID NO: 26) | 63.6 |
| 11R | GGCAGGCGGCAACGTCTCAA (SEQ ID NO: 27) | 63.4 |
| 12F | CGTGATTGGCGCCTGGCTGA (SEQ ID NO: 28) | 63.2 |
| 12R | TGCGCACGGCAAGCATGTTC (SEQ ID NO: 29) | 62 |
| 13F | CAGGGAGAACGACCTGCGCC (SEQ ID NO: 30) | 63.2 |
| 13R | CTGGCGAGGCCAGTTGACCG (SEQ ID NO: 31) | 63.6 |
| 14F | CGCAATGTCGTGCCACCCGA (SEQ ID NO: 32) | 63.3 |
| 14R | GGCGAGAGCGTGGCAGTTCA (SEQ ID NO: 33) | 62.8 |
| 15F | TTCCGCCGTCTGACCACCCA (SEQ ID NO: 34) | 63.8 |
| 15R | GCTTTGCCTGGTCGCTTGCC (SEQ ID NO: 35) | 62.5 |
| 16F | CGACCCGAAGGCCGCTCTTT (SEQ ID NO: 36) | 62.6 |
| 16R | ACCGCCTGGTCAAGGGAGCA (SEQ ID NO: 37) | 64 |
| 17F | TGCCAGCAGCGTATTCGGCG (SEQ ID NO: 38) | 63.3 |
| 17R | TTCTGCCCGGTCGGCTTTGC (SEQ ID NO: 39) | 63.5 |

Kits

The invention also provides a diagnostic pack or kit comprising one or more containers filled with one or more of the diagnostic reagents described herein. Such diagnostic reagents include fragments and oligonucleotides useful in the detection of SEQ ID NO: 1+ bacteria in a subject or sample isolated therefrom. Diagnostic reagents may comprise moiety that facilitate detection and/or visualization. Diagnostic reagents may be supplied in solution or immobilized onto a solid phase support. Optionally associated with such container(s) are buffers for performing assays using the diagnostic reagents described herein, negative and positive controls for such assays, and instructional manuals for performing assays.

Unless defined otherwise, all technical and scientific terms used herein have the same meaning as commonly understood by one of ordinary skill in the art to which this invention belongs.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

All publications mentioned herein are incorporated herein by reference to disclose and describe the methods and/or materials in connection with which the publications are cited.

EXAMPLES

Although genes contribute to RA susceptibility, genetic effects appear to require environmental factors in order to explain differences in incidence of the disease. Environmental risk factors associated with RA development include smoking and infection. One of the more intriguing environmental covariates modulating autoimmunity is the intestinal microbiota. The human intestine contains $10^{13}$-$10^{14}$ microorganisms whose collective genome (microbiome) is ≥100 times larger than the human host. Human intestinal tract bacteria are exceptionally dense and diverse, encompassing hundreds of species (>80% still uncultured). Gnotobiotic mouse models—comparing animals reared germ-free, or with defined subpopulations of normal mouse or human gut microorganisms—suggest that the gut microbiome modulates both the maturation and activity of the innate and adaptive immune systems. It is plausible, therefore, that undesirable microbiomes might have untoward immunological effects. In patients with inflammatory arthritis, fragments of normal intestinal bacteria (cell wall products/nucleic acids) are detected in the inflamed joints [Severijnen et al. J Rheumatol, 1989. 16(8): 1061-8; van der Heijden et al. Arthritis Rheum, 2000. 43(3): 593-8], and concordant T cell skewing in the gut and joints has been reported [Hirota et al. J Exp Med, 2007. 204(12):2803-12]. In animal models, parenteral injection of cell wall fragments from several intestinal bacteria induces joint inflammation, and some commensal gut microbiota cause experimental arthritis [Severijnen et al. J Rheumatol, 1989. 16(8): 1061-8]. In our current investigations on the role of oral and gut microbiome in RA, the present inventors have found that new-onset, DMARD-naive RA (NORA) patients have a particular bacterial pattern dominated by the high prevalence and abundance of a particular operational taxonomic unit (OTU), which defines a bacterial species designated herein as SEQ ID NO: 1+ bacteria, a bacterium closely related to intestinal *Prevotella*.

Patients and Methods and Materials

Study Participants.

Consecutive patients from the NYU Rheumatology clinics and offices were screened for the presence of RA and offered enrollment. After informed consent was signed, past medical history (chart review and interview/questionnaire), diet and medications were determined. A screening musculoskeletal exam and laboratory assessments were also performed or reviewed; all RA patients who met study criteria were offered enrollment.

Inclusion criteria involved RA patients meeting 2010 ACR/EULAR criteria for RA, including presence of rheumatoid factor (RF) and/or anti-citrullinated peptide antibodies (ACPA), and age 18 years or older. New-onset rheumatoid arthritis (NORA) was defined as disease duration of >6 weeks and absence of any treatment with disease-modifying anti-rheumatic drug (DMARD) or steroids (ever). Chronic-established RA (CRA) was defined as any patient meeting criteria for RA with minimum disease duration of 6 months. Most CRA subjects were receiving DMARDs (oral and/or biologic agents) and/or corticosteroids at the time of enrollment. Healthy controls were age-, sex- and ethnicity-matched individuals with no personal history of inflammatory arthritis.

Exclusion criteria for all groups were: recent (<3 months prior) use of any antibiotic therapy; current extreme diet (parenteral nutrition, macrobiotic diet, etc.); known inflammatory bowel disease; known history of malignancy; current consumption of probiotics; any GI tract surgery leaving permanent residua (e.g., gastrectomy, bariatric surgery, colectomy); significant liver, renal or peptic ulcer disease. This study was approved by the Institutional Review Board (IRB) of New York University School of Medicine, and all participants provided written informed consent prior to initiation of the study available for the analyses presented here.

Sample Collection and DNA Extraction.

For microbiota analysis, fecal samples were obtained from all enrollees and processed. Samples (~100 gm) were collected per protocol. Aliquots of all samples have been sent to MSKCC for genomic analysis. Each sample was directly suspended in MoBio buffer containing tubes (Mo-Bio). DNA was extracted within 1 hr of sample collection using a combination of the MoBio Power Soil kit (MoBio) and a mechanical disruption (beadbeater) method based on a previously described protocol (Costello et al. Science 2009; 326:1694-7). Samples were stored at −80° C.

V1-V2 16S rRNA Region Amplification and 454/Pyrosequencing.

For each sample, 3 replicate 25-µl PCRs were performed, each containing 50 ng of purified DNA, 0.2 mM dNTPs, 1.5 mM MgCl2, 1.25 U Platinum Taq DNA polymerase, 2.5 µl of 10×PCR buffer, and 0.2 µM of each primer designed to amplify the V1 and V2 regions as previously described (Turnbaugh et al. Nature 2009; 457:480-4): a modified primer 8F (5'- CTATGCGCCTTGCCAGCCCGCTCAG-

TCAGAGTTTGATCCTGGCTCAG-3'; SEQ ID NO: 4)

composite of 454 primer B (underline), linker nucleotides (TC), and the universal bacterial primer 8F (italics); and the modified primer 338R (5'-

CGTATCGCCTCCCTCGCGCCATCAGNNNNNNNNNNNNCAGCTGCCTCCCG

TAGGAGT-3'; SEQ ID NO: 5)

composite of 454 primer A (underline), a unique 12-base barcode (Ns), linker nucleotides (CA), and the broad-range bacterial primer 338R (italics). Replicate PCRs were pooled, and amplicons were purified using the Qiaquick PCR Purification Kit (Qiagen). PCR products were sequenced on a 454 GS FLX Titanium platform following the 454 Roche recommended procedures.

Sequence Analysis.

Sequence data were compiled and processed using mothur (Schloss et al. Appl Environ Microbiol 2009; 75:7537-41). Sequences were converted to standard FASTA format. Sequences shorter than 200 bp, containing undetermined bases or homopolymer stretches longer than 8 bp, with no exact match to the forward primer or a barcode, or that did not align with the V1-V2 regions were not included in the analysis. Using 454 base quality scores, which range from 0-40 (0 being an ambiguous base), sequences were trimmed using a sliding-window technique, such that the minimum average quality score over a window of 50 bases never dropped below 30. Sequences were trimmed from the 3'-end until this criterion was met. Sequences were aligned to the V1-V2 region of the 16S gene, using as template the SILVA reference alignment (Pruesse et al. Nucleic Acids Res 2007; 35:7188-96) and the Needleman-Wunsch algorithm with the default scoring options. Potentially chimeric sequences were removed using the ChimeraSlayer program (Haas et al. Genome Res 2011; 21:494-504). To minimize the effect of pyrosequencing errors in overestimating microbial diversity (Huse et al. Environ Microbiol 2010; 12:1889-98), low abundance sequences that differ in 1 or 2 nucleotides from a high abundant sequence were merged to the high abundant sequence using the pre cluster option in mothur. Sequences were grouped into operational taxonomic units (OTUs) using the average neighbor algorithm. Sequences with distance-based similarity of 97% or greater were assigned to the same OTU. For each fecal sample, OTU-based microbial diversity was estimated by calculating the Shannon diversity index and the Simpson diversity index (Magurran. Measuring Biological Diversity. Oxford, UK: Blackwell Publishing; 2004). OTU-based microbial richness was estimated using the Chao index. Phylogenetic classification was performed for each sequence, using the Bayesian classifier algorithm described by Wang and colleagues with the bootstrap cutoff 60% (Wang et al. Appl Environ Microbiol 2007; 73:5261-7).

Tree Building and UniFrac Clustering for PCA Analysis.

A phylogenetic tree was inferred using clearcut (Evans et al. J Mol Evol 2006; 62:785-92) on the 16S sequence alignment generated by mothur. Unweighted UniFrac was run using the resulting tree (Lozupone et al. BMC Bioinformatics 2006; 7:371). PCA was performed on the resulting matrix of distances between each pair of samples.

Statistical Analyses.

To determine whether there were statistically significant differences between samples from disease and healthy individuals, bacteria with less than 5 mean count in both conditions were removed, and t-test was applied to log 2 transformed scaled count-data. The count data was rescaled using DESeq R package (Anders et al. Genome Biol 2010; 11:R106). To adjust for multiple hypothesis testing, the False Discovery Rate (FDR) approach of Benjamini and Hochberg (Benjamini et al. J Royal Stat Society Series B 1995; 57:289-300) was employed, and used fdr.R package. The final results were filtered for p value <0.05 and a FDR ≤0.1. For cross-sectional analyses of baseline characteristics, differences were evaluated using Student's t test, Mann-Whitney U test or chi-squared tests, when appropriate. SPSS V.16.0 software (SPSS, Chicago, Ill., USA) was used for the analysis, two-tailed significance testing was employed and significance was set as p<0.05.

The above protocols were performed as described in Scher et al. (Arthritis Rheum. 2012 October; 64(10):3083-94. doi: 10.1002/art.34539), the entire contents of which is incorporated herein in its entirety, including the references cited therein.

Results

Nucleic Acid Extraction, 16S rRNA Gene Amplification, Purification and 454 Sequencing.

DNA is extracted from stool per protocol and variable 16S rRNA gene regions are amplified by PCR using primers flanking the V1-V2 hypervariable region. PCR products are sequenced in the Genomics Core using the 454 Titanium Platform and DNA sequences and compared to sequence catalogues by the Ribosomal Database Project (RDP) by BLAST. Phylogenetic trees from the rDNA sequences are then generated and the UNIFRAC metric used to compare bacterial communities in different individuals. This matrix can be used with multivariate statistical techniques such as Principal Components Analysis (PCA), which plots the components that explain most of the variation observed between samples. UniFrac can also perform a P-test to indicate whether differences in the flora of two individuals can be explained by chance. All analyses are performed on 12,500 DNA sequences per sample obtained by 454 sequencing. This approach was used to assess whether overall microbial diversity, or the relative representation of different bacterial families or phyla, is associated with the presence of RA.

To this end, phylum- and family-level taxonomic assignments are determined and quantified for each clinical sample. Phylogenetic diversity curves (plotting diversity versus increasing numbers of obtained sequences) and rarefaction curves (plotting number of operational taxonomic units against number of sequences) are generated for each clinical sample. Microbial diversity and the relative representation of different phyla and family are determined for patients with and without NORA. Shannon diversity and equitability indices for each sample will be determined using spreadsheet software.

To look for specific bacterial species associated with NORA, the present inventors used PCA and hierarchical clustering to identify potential differences between the microbial flora of patients with NORA and controls. Using this approach, bacterial species that were more prevalent in patients with NORA were catalogued. The present inventors performed the P-test with 1000 permutations to determine whether differences in the flora can be explained by chance. Using this approach, studies presented herein reveal intestinal microbiome parameters associated with NORA, which are described in greater detail herein below (See also FIG. 3A-C).

As described herein, the present inventors have generated a partial genome sequence of a bacterial species designated herein as SEQ ID NO: 1+ bacteria. In brief, microbial DNA from a previously identified human fecal sample containing a 68% abundance of SEQ ID NO: 1+ bacteria (by 16S sequencing) was extracted, purified, and sequenced on the 454 GS FLX Titanium platform. A total of 1.2 million reads were assembled into 132 contigs at an average depth of coverage of 20×. Comparison of these contigs to sequenced *Prevotella* genomes with BLAST revealed SEQ ID NO: 1+ bacteria to be approximately 68% identical to *P. copri*, strongly suggesting that it is a novel strain of this organism.

*P. copri* is a recently described [Hayashi et al, 2007, International Journal of Systemic and Evolutionary Microbiology 57:941-946] member of the human intestinal microbiome and literature lacks data regarding its molecular and enzymatic properties. Paired-end sequencing and analysis of both *P. copri* and SEQ ID NO: 1+ bacteria will be necessary to identify genomic differences responsible for SEQ ID NO: 1+ bacteria's segregation with arthritic phenotypes in humans. While *P. copri* remains largely uninvestigated, the genus *Prevotella* has been found to be elevated in intestinal microbiome studies of other autoimmune disorders such as Inflammatory Bowel Disease (IBD) [Lucke et al. J Med Microbiol. 2006. 55(Pt 5):617-24. Interestingly, Flavell et al. have demonstrated a pathogenic role of intestinal *Prevotella* in a mouse model of colitis [Elinav et al. Cell, 2011. 145(5):745-57. Epub 2011 May 12]. Furthermore, the colitis phenotype can be "transmitted" to wild-type animals in co-housing experiments and is linked to the presence of *Prevotella*.

Further to the above and because protein-coding genes of importance may exist in gaps between contigs, the present inventors are in the process of obtaining complete genomes of both *P. copri* and SEQ ID NO: 1+ bacteria to ensure that no potential genes of interest remain unanalyzed. Paired-end sequencing followed by targeted long-range PCR will be used to span current gaps in both sets of sequences and prepare the genomes for downstream analyses. Utilizing similar bioinformatic tools as those employed for the SFB genome [Sczesnak et al. Cell Host Microbe, 2011. 10(3): 260-72; the entire contents of which is incorporated herein in its entirety], the present inventors are working to identify (1) organisms with similar metabolic potential to SEQ ID NO: 1+ bacteria, (2) candidate pathways for investigation of SEQ ID NO: 1+ bacteria's putative modulation of the immune system in arthritis, (3) metabolic pathways that may reveal optimal culture conditions for this as-yet uncultured microbe, and (4) SEQ ID NO: 1+ bacteria-specific genome primer sets to aid in its rapid identification in patients.

It is, moreover, noteworthy that two studies have recently reported the presence of *Prevotella* species in the serum and synovial fluid of active RA patients [Martinez-Martinez et al. J Clin Periodontol, 2009. 36(12):1004-10; Moen et al. Clin Exp Rheumatol, 2006. 24(6):656-63]. Although not confirmed, these reports suggest that overrepresentation of certain intestinal bacteria in anti-citrullinated-peptide antibody positive (ACPA+) NORA individuals may be regarded as the "second event". Based on results presented herein, the present inventors suggest that in response to such microbial burden, certain predisposed individuals develop inflammatory disease at clinical onset and that SEQ ID NO: 1+ bacteria can be pathogenic for RA development and utilized as a predictive biomarker for disease.

SEQ ID NO: 1+ Bacteria as Pathogenic Factor and Predictive Biomarker in Rheumatoid Arthritis.

The present inventors suggest herein that the presence and abundance of SEQ ID NO: 1+ bacteria serves as a triggering factor for breaking tolerance and drives, at least in part, autoimmune processes in Rheumatoid Arthritis (RA) via arthritogenic products unique to this bacterium. The present inventors have made the novel discovery that a specific bacterial species, closely related to intestinal *Prevotella* (herein SEQ ID NO: 1+ bacteria) is present at significantly higher prevalence and abundance in the gut microbiome of ACPA+ NORA patients compared to healthy individuals and chronic-treated RA patients (FIGS. 3A-C). The present inventors have, moreover, demonstrated that DMARD naive NORA patients exhibit a distinct intestinal microbiome, characterized by an unexpectedly high abundance of SEQ ID NO: 1+ bacteria. The SEQ ID NO: 1+ bacterial species was identified as a particular operational taxonomic unit (OTU). OTU defines the terminal node in phylogenetic analysis and refers roughly to a species-level microorganism found through 16S sequencing. OTUs are, by convention, at least 97% unique compared to other species analyzed in a given community of bacteria, which in the present case is the gut microbiome. In the cohort examined herein, more than 75% of anti-citrullinated-peptide antibody positive (ACPA+) NORA patients exhibited SEQ ID NO: 1+ bacteria compared to less than 15% in controls (p<0.001) (FIG. 3).

Noticeably, recent literature shows that the composition of the adult human gut microbiome can be classified into just three distinct and stable combinations (enterotypes) that appear across populations from a variety of backgrounds. These enterotypes are dictated by the bacterial species present and are independent of individual host properties. *Prevotella*, the predominant bacteria in enterotype 2, is present in only 13% of people [Arumugam et al. Nature, 2011. 473(7346):174-80. Epub 2011 Apr. 20].

Full Genome Characteristics of Candidate Bacteria (SEQ ID NO: 1+).

The present inventors predict that SEQ ID NO: 1+ bacteria comprises virulent factors with pro-inflammatory and arthritogenic properties. This prediction is analogous to the inventors' previously published observations that both pro-inflammatory Th17 cells and bacterial exposure (segmented filamentous bacteria) play critical roles in the initiation of inflammatory arthritis (K/BxN mouse model; Wu et al., 2010, Immunity 32:815-827). Identifying and characterizing SEQ ID NO: 1+ bacteria sequences and components, enzymatic properties, and nutritional requirements will provide a deep understanding of: a) bacterial behavior and its interaction with other intestinal microbiota, b) presence of potential pro-inflammatory (with local and/or systemic effects) molecules amenable for targeting, and c) mechanistic processes involved in microbe-host interactions in mice and in predisposed animal models of RA-like disease. This would allow for potential discoveries regarding etiopathogenesis and mechanisms of disease, which would be similar to those derived from the observation of peptidyl arginine-deiminase in *Porphyromonas gingivalis* and its relationship to peptide citrullination [Wegner et al. Immunol Rev. 2010. 233(1):34-54].

This invention may be embodied in other forms or carried out in other ways without departing from the spirit or essential characteristics thereof. The present disclosure is therefore to be considered as in all aspects illustrate and not restrictive, the scope of the invention being indicated by the appended claims, and all changes which come within the meaning and range of equivalency are intended to be embraced therein.

What is claimed is:

1. A method for diagnosing and treating new onset rheumatoid arthritis (NORA) in a subject, the method comprising:
   a) obtaining a biological sample from the subject;
   b) detecting in the biological sample an increased amount of a *Prevotella*-related species of bacteria relative to that of a biological sample obtained from a control subject, wherein the *Prevotella*-related species of bacteria comprises SEQ ID NO: 1 or a variant thereof SEQ ID NO: 2 or SEQ ID NO: 3, thereby diagnosing NORA in the subject; and
   c) administering a nonsteroidal anti-inflammatory drug (NSAID), a disease-modifying anti-rheumatic drug (DMARD), a steroid, an antibiotic, or an analgesic to the subject diagnosed with NORA.

2. The method of claim 1, wherein the subject has a familial history of RA and/or exhibits at least one of the seven diagnostic criteria used to diagnose RA selected from the group consisting of morning stiffness in and around joints lasting at least 1 hour before maximal improvement; soft tissue swelling of 3 or more joint areas observed by a physician; swelling of the hand joints; symmetric swelling; rheumatoid nodules; elevated levels of serum rheumatoid factor (RF); and radiographic changes in hand and/or wrist joints.

3. The method of claim 1, wherein the biological sample is fecal material, biopsies of specific organ tissues, synovial fluid, or synovial fluid biopsies.

4. The method of claim 3, wherein the specific organ tissues comprise large and small intestinal biopsies.

5. The method of claim 1, wherein the amount of the *Prevotella*-related species of bacteria is determined by nucleic acid sequencing.

6. The method of claim 5, wherein the nucleic acid sequencing is massively parallel 16S rRNA pyrosequencing.

7. The method of claim 5, wherein the nucleic acid sequencing detects 16S rRNA comprising SEQ ID NO: 1, SEQ ID NO: 2, or SEQ ID NO: 3 and the amount of the 16S rRNA comprising SEQ ID NO: 1, SEQ ID NO: 2, or SEQ ID NO: 3 is indicative of the amount of *Prevotella*-related species of bacteria in the biological sample.

8. The method of claim 1, wherein the *Prevotella*-related species of bacteria is *P. copri*.

9. The method of claim 1, wherein the amount of the *Prevotella*-related species of bacteria is detected using a reagent that specifically binds to the *Prevotella*-related species of bacteria or a nucleic acid sequence thereof.

10. The method of claim 9, wherein the reagent is selected from the group consisting of an antibody, an antibody derivative, an antibody fragment, a nucleic acid probe, an oligonucleotide, and an oligonucleotide primer pair specific for *Prevotella*-related species of bacteria comprising SEQ ID NO: 1, SEQ ID NO: 2, or SEQ ID NO: 3.

11. The method of claim 9, wherein the reagent is an oligonucleotide primer pair of SEQ ID NO: 4 and SEQ ID NO: 5.

12. The method of claim 9, wherein detecting of the increased amount of the *Prevotella*-related species of bacteria includes at least one assay selected from the group consisting of nucleic acid sequencing, PCR amplification, a competitive binding assay, a non-competitive binding assay, a radioimmunoassay, immunohistochemistry, an enzyme-linked immunosorbent assay (ELISA), a sandwich assay, a gel diffusion immunodiffusion assay, an agglutination assay, dot blotting, a fluorescent immunoassay such as fluorescence-activated cell sorting (FACS), a chemiluminescence immunoassay, an immunoPCR immunoassay, a protein A or protein G immunoassay, and an immunoelectrophoresis assay.

13. The method of claim 1, further comprising processing the biological sample and analyzing the processed biological sample generated thereby to determine the amount of *Prevotella*-related species in the biological sample.

14. The method of claim 13, wherein the processing comprises extracting nucleic acids from the biological sample.

15. The method of claim 1, further comprising obtaining a sample of T cells from the subject to identify T cells specific for the *Prevotella*-related species of bacteria in the subject.

16. The method of claim 1, wherein the disease-modifying anti-rheumatic drug (DMARD) is methotrexate.

* * * * *

UNITED STATES PATENT AND TRADEMARK OFFICE
CERTIFICATE OF CORRECTION

PATENT NO. : 10,011,883 B2
APPLICATION NO. : 14/351622
DATED : July 3, 2018
INVENTOR(S) : Steven B. Abramson et al.

Page 1 of 1

It is certified that error appears in the above-identified patent and that said Letters Patent is hereby corrected as shown below:

In the Specification

At Column 1, Lines 19-21, replace:
"This invention was made with government support under RC2 AR059896 awarded by the National Institutes of Health. The government has certain rights in the invention."

With:
--This invention was made with government support under grant number AR058986 awarded by the National Institutes of Health. The government has certain rights in the invention.--

Signed and Sealed this
Fourteenth Day of May, 2019

Andrei Iancu
*Director of the United States Patent and Trademark Office*

SEQUENCE LISTING

```
<160> NUMBER OF SEQ ID NOS: 85

<210> SEQ ID NO 1
<211> LENGTH: 182
<212> TYPE: DNA
<213> ORGANISM: Prevotella copri

<400> SEQUENCE: 1
gcgaaagtaa gactaatgcc caatgacatc tctagaagac atctgaaagg gattaaagat      60
ttatcggtga tggatgggga tgcgtctgat tagcttgttg gcggggtaac ggcccaccaa     120
ggcgacgatc agtaggggtt ctgagaggaa ggtcccccac attggaactg agacacggtc     180
ca                                                                    182

<210> SEQ ID NO 2
<211> LENGTH: 182
<212> TYPE: DNA
<213> ORGANISM: Prevotella copri

<400> SEQUENCE: 2
gcgaaagtaa gactaatacc caatgacgtc tctagaagac atctgaaaga gattaaagat      60
```

```
ttatcggtga tggatgggga tgcgtctgat tagcttgttg gcggggtaac ggcccaccaa      120
ggcgacgatc agtaggggtt ctgagaggaa ggtcccccac attggaactg agacacggtc      180
ca                                                                      182

<210> SEQ ID NO 3
<211> LENGTH: 182
<212> TYPE: DNA
<213> ORGANISM: Prevotella copri

<400> SEQUENCE: 3
gcgaaagtaa gactaatacc caatgatatc tctagaagac atctgaaaga gattaaagat       60
ttatcggtga tggatgggga tgcgtctgat tagcttgttg gcggggtaac ggcccaccaa      120
ggcaacgatc agtaggggtt ctgagaggaa ggtcccccac attggaactg agacacggtc      180
ca                                                                      182

<210> SEQ ID NO 4
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 4
ctatgcgcct tgccagcccg ctcagtcaga gtttgatcct ggctcag                     47

<210> SEQ ID NO 5
<211> LENGTH: 57
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (26)..(37)
<223> OTHER INFORMATION: n is adenine or guanine or cytosine or
      thymidine/uracil

<400> SEQUENCE: 5
cgtatcgcct ccctcgcgcc atcagnnnnn nnnnnnncag ctgcctcccg taggagt         57

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
cgccctcgtt gccactggag                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
ttgaaatccg gcaggcggca                                                   20

<210> SEQ ID NO 8
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 8
agggagaacg acctgcgcct                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
ggcacacggg ttgagcggaa                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
tctgccacca cgtcctcgct                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
agccgactaa cccaggcggt                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
cctacgatgg cgcacagggc                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
tcgccgaata cgctgctggc                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (11)..(11)
```

<223> OTHER INFORMATION: n is inosine

<400> SEQUENCE: 14
tgcgatgcac ntgccaccga					20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
gatggcagcc ttgtcgcggt					20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
gtcgccgggg cggtttcttt					20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
tgttcgttgc gccccttgct					20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
cccacgatgg gcatcagccg					20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
gtcgcttgcc agggcgttca					20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
caccgcctgg gttagtcggc					20

```
<210> SEQ ID NO 21
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 21
aggtcaggcg ctgctttgc                                                   19

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
agcaacgcca cgaagctggt                                                  20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
tcagccaggc gccaatcacg                                                  20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
tgcgcagaaa cggcaaggga                                                  20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
tggcagccat gctgtacgcc                                                  20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
gtccgccctc gttgccactg                                                  20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 27
ggcaggcggc aacgtctcaa                                        20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
cgtgattggc gcctggctga                                        20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
tgcgcacggc aagcatgttc                                        20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
cagggagaac gacctgcgcc                                        20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
ctggcgaggc cagttgaccg                                        20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
cgcaatgtcg tgccacccga                                        20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
ggcgagagcg tggcagttca                                        20

<210> SEQ ID NO 34
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 34
ttccgccgtc tgaccaccca                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
gctttgcctg gtcgcttgcc                                              20

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
cgacccgaag gccgctcttt                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
accgcctggt caagggagca                                              20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
tgccagcagc gtattcggcg                                              20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
ttctgcccgg tcggctttgc                                              20

<210> SEQ ID NO 40
<211> LENGTH: 651
<212> TYPE: DNA
<213> ORGANISM: Prevotella copri

<400> SEQUENCE: 40
atggacgatg aacgactcaa aaatcttggt ggtggtaact attggaaaga gttgctcgac     60
```

```
cgtattcgtg atattcgttc atcagaaaag gtgctttatc gacaagttct ggacatctat    120
gccacaagtg ttgactatga ccctcgaact gatgcctcaa agcttttctt taaaatcgtg    180
caaaataagt tgcactatgc tgctcatggg catacagcgg cagaagttat ctatgagcgt    240
gcggatgccg acaaaccatt tatgggcttg acgacatttg agggcgaact gccagctatc    300
aaagacatca aaatagccaa gaactatctg aaagaaaatg agctgaagat actcaataat    360
cttgtttccg gttattttga ttttgccgag attatggcaa tggagcatcg cccagtctat    420
atgatggatt atgtgaaaca acttgatact atcctgcaat ccacagggcg acctttgttg    480
aaggggtcgg gaagtatcag ccatgaagag gcaatggaca aagctatagc tgagtatcga    540
aaatatcagg taaggtatt aactccagta gaggaggctt atcttgaatc catcaatgct    600
ttgggaaaaa ttgcaaagcg caagggaaga caatcggggg aaaatcatta a             651
```

```
<210> SEQ ID NO 41
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 41
atggacgatg aacgactcaa aaatct                                          26

<210> SEQ ID NO 42
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 42
ttaatgattt tccccgatt gtcttc                                           26

<210> SEQ ID NO 43
<211> LENGTH: 933
<212> TYPE: DNA
<213> ORGANISM: Prevotella copri

<400> SEQUENCE: 43
atggataaac tcgtagagcg aaccaacgga gccatcacca agcagagcat ctcccgatat     60
gagaaaggca tcatgcgccc taagcgtgat gccctgcaag ccatagccaa agccctcaat    120
atcagcgagg aatatttcga aggaaccaat ctcaagatag atatgcctat gctccgcacc    180
acctccagtg gcaagttgtc cgaagacgag ttgcaagccc tggaagcaaa actctcgttt    240
tgggcagagc agtatcttac gaaggagaaa gaagcaggct ttcctacccg gttcaagaat    300
ccggtaaaag gcaccaaggt atcaacccctt gaagatgcca tccatgctgc cgaccttctt    360
cgtgaaaagt ggtattgcgg tgatggacct atcgccagta tcctgagact cttggaaaga    420
aaaggtatca tgatacttgc tgcaactctc ccggattatg tcttcggaat gagcacctgg    480
gcagataaga agcatccgct gatgattctc gatttcaatc cggaaaagag tagcgtagag    540
aaacttcgct tcacggcagt tcatgaactg gcccatctgc ttctcctctt cccggaagat    600
agtccgctga ggctggagaa gcgttgtgat ctctttgcca gtttcttcct tcttcctaaa    660
ttggcgctta tcgaagagtt gggttccaag aaacgtgaga agataacgct ggaggagatg    720
attgacatca aggaactgta tggcgcatct ctcgccgcat ccatcatcgc cgcagggat    780 tatggcatta tcaccaccga gtataaacgt gcatggtatg ccgagcatat agagcctaat    840
```

```
cctcgagaaa taggtaatgg ccactatgca tttcctgaga cattgggaag ggagaagaga    900
gtcaactcaa tcatcaaaag tatggaggaa tag                                 933
```

<210> SEQ ID NO 44
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 44

```
atggataaac tcgtagagcg aaccaa                                          26
```

<210> SEQ ID NO 45
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 45

```
ctattcctcc atactttga tgattg                                           26
```

<210> SEQ ID NO 46
<211> LENGTH: 570
<212> TYPE: DNA
<213> ORGANISM: Prevotella copri

<400> SEQUENCE: 46

```
atggagaatg gcgaagttgt gactcgccct gaatacctca tcctccctgc caccttcggc    60
atgtggatga tggtgatggt actctacatc ttctcaacca agaacggatg taacttcatc   120
aactggtggc agcgtgttct tttccgttcc agcaagaata agattgccgc ccgtccgatg   180
acacatcata caagtatcgt caccttcatg gaactgaaca tgattctctg gaccagctat   240
ctcctgttga tgttctgcta cgacaagaat ttcctcggcg accatcaccc tgtaacttcg   300
gttgttgccg cagcttgtct gataggtagt ttcttcatct tccgaaagca gttgcgtttg   360
agcacatggg gagcaaacat ccgtatggct atcgcaacgg ttgtcgtgtt ctgggtacct   420
gtggaagtgc ttggtcgctt ggacttttc aaggagattt ggattgagcc agagaagtat   480
atcacccaga tgatctgcat cctcgtggca ttcgtggcat tgctcgtcta tatcatgata   540
gtatctaaaa agaagaagac acatgagtaa                                    570
```

<210> SEQ ID NO 47
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 47

```
atggagaatg gcgaagttgt gactcg                                         26
```

<210> SEQ ID NO 48
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 48

```
ttactcatgt gtcttcttct ttttag                                          26
```

<210> SEQ ID NO 49
<211> LENGTH: 1320
<212> TYPE: DNA
<213> ORGANISM: Prevotella copri

<400> SEQUENCE: 49

```
atgaagttct tggaagaca aaacgaaata aaagaattgc aagagataag aaatctatct      60
ttgcaaacgg cccgttttac aatcgtaacc ggacgccgac gtagcggtaa gacatcctta    120
ttgataaaag catacgagga tgttcaggat atgctgtatt ctttgttgc aagaaaatca     180
gaagcagaac tctgcagaga ttttatcgaa gagatgacga ccaaacttca gcttcctatt    240
ctcggtgaag taacacgctt tgctgacatc tttaaatatc tgcttcaact atccaagatt    300
cgccctatca ctctcatcat tgatgagttt caggatttca agcgggttaa tccatcaatc    360
ttttcagata tgcaaaagat atgggaccct aacaaacagg aagctcatat taatcttgtg    420
gtctgcggtt ctgtttattc acttatgaac atcatcttta aaataacaa gcaaccactt     480
tatggcaggc agactggaga aataaaaagtc actccatttc cccttctgt cattaaggaa    540
attctctcta catataattc tgcctatacc aatgatgacc tactggctct ctacagttat    600
acaggcggag tagcagaata tgtagaaatg atgatggatg caggagccac gaccaaggaa    660
cagatgacag agcggtttat tgcaaaaaac tcttatttca tctacgaagg aaaaaatatg    720
ctgatagaag aatttggcaa agactatgcc cgctatttcg agatactgca acttatcgct    780
tcaggctaca caactcgagg tgaaatagaa agcatcatga aaatagaact ttcgggctat    840
ctcaccaaac tggagaacga ctatagcttg atctcccgtt atataccgat gttccaaaag    900
accaatcgca acattcgcta tcagatagaa gacaacttcc ttcgcgtctg gtttcgctac    960
atctacaaat atggatacat gatagaggtt ggcgccaata aaaaactaaa aatggtcatg   1020
gataagagct acaccacata caccggcaag gttctggaaa gatattttat tgccaagatg   1080
atagagagcg aagaatatac ccagatagcc tcctggtggg acagaaaggg agagaatgaa   1140
atcgatatta tcgctgccga tgaactggag cagaaggtta ttttttatga ggtaaaacgc   1200
caagctaagg atataaaatct cggcatttta aaagataaag ccgagcattt cttccaagct   1260
acaggaaaat tcaagaaatt cgatatcgga taccaaggat tgtcgatgga ggatatgtaa   1320
```

<210> SEQ ID NO 50
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 50

```
atgaagttct ttggaagaca aaacga                                          26
```

<210> SEQ ID NO 51
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 51

```
ttacatatcc tccatcgaca atcctt                                          26
```

```
<210> SEQ ID NO 52
<211> LENGTH: 603
<212> TYPE: DNA
<213> ORGANISM: Prevotella copri

<400> SEQUENCE: 52
ttggtagtag atgagagtgg cagcatgagc attatcgagc gccaggcact ggtgggcatc     60
aacgagaccc tgaccacgat tcagaaaatg cagaagacgc ataagaacat ggagcagcgt    120
gtaacgctca ttaccttcga cagcacccac aagaagctgt tctacgataa tgtgtctgcc    180
cgccatgcca cccatttgac ctcaagggat tacaacccat gtggcggcac ccctctttat    240
gatgccatag gtatgggtat agccaagatc aatgccctga ccaccgagga tgacagcgta    300
ttggtaacca tcattacgga tggtgaggag aactgcagcg aggagtatga tttgaagatg    360
atcaagaacc tcattgagaa gctgaagaaa cagaactgga cctttacctt tatcggcacc    420
gatgaccttg atgtggaaaa cattgctctt gatatgggaa tcgacaacca cctgcagttc    480
tcggaagatg aggctggcac cagggcgatg tttgcaagag aaaacagagc ccgagagcgc    540
tacaacaagt gccgtgcgat ggattgcaag atggaagctg ggagttactt tgaggagaaa    600
taa                                                                 603

<210> SEQ ID NO 53
<211> LENGTH: 1782
<212> TYPE: DNA
<213> ORGANISM: Prevotella copri

<400> SEQUENCE: 53
gtgaaaatac tactattatt tagaccccat tttattataa atataatata tatacctgat     60
aatcagttgt attgtgcttt tctgcagact ttgtatttta gaccctattt agttctatta    120
ttgaaaaata ttttgtattt ttgcgccctg aatgtaatta tactaaatat gagaagaagt    180
atttcgttta cgatattgtt ttttatgatg ctttcggtgt tggtatcatg ttatcaaagt    240
cataagagag agttagactt agcttatacg ttggcagagt ctaagcctga tagtgccttg    300
gcctttttga accgtatcaa tcaaggtaaa ctctcagata agatatggc gaagtatgcc     360 ctcacttatt atatggcaca agacaagtct ggcttagatg tggataacga ttctttgatt    420
cgcatagcgt atgattggta tggagaacat caggacgatt ctctttatgc ttcatccttg    480
tattatatgg gaaaatgctt tctgctgaat gatagtatgg agcaggctaa ggcatgtttg    540
gagaaatctt attctatttc agacagtctt cataatctga gcttaaaatg cttggcattg    600
gataagctga tagaagtaga agaacaactg gcaccttaca aagcgttgaa ctatgctaaa    660
gctttggtga agatgtatga gtccatgcca aatgttagta tataataa ggtggcagcg      720 catttgaggt taggggagaa cttctttat gttgatagtt tgaaacaagc tttgaacgaa     780
gagaaaaagg catataggtt ggcgatatat gcaaacgata tgaattgct gtcaagtgta     840 aaacaaaatt tggctagtac gtttgaggaa atggagaaa aggatagttg tctgctttat     900
gctcaacaag cctatgggtt acaaggtgca agtagttttt cttgtcaact aaatctagcc    960
ttggcttata tttctgtcga ttctataaaa caagcttttg tcttgttgga tcaagcaact   1020
cctaaaactg ctgaagatca ttattcgata ttttatatga aagtaaagc agctatgaaa    1080 gctcaagatt ataagatggc taaaaccttt agtgattctg catgttgtta cttgcaagaa   1140
atgtaccgaa cagcatccaa agccaagatt tcctattaca cttcattctt gaagaaagaa   1200
agcgaaaggg caagaataca aggtaaggct gaaatgcagc gatgggtatt tggattgaca   1260
```

```
gtacttttat gcttgataat tattttgttt gtcttgtatg cttattggtc gtatcgaaaa    1320
ctgtcattag ctcgcatagc tcatgaacag gaaatattca cccaaaagca gcaaatgatg    1380
gagaaattac accaagaaga actctcgcat agggatgtgc aattgtctgt aatgcgtacc    1440
tatttactaa agaagataga ggttgtggaa aaattaaatt cgagtgttcc gaatgagagt    1500
aagcatattg tgctttccga taatgattgg acagagttag aagtcttctt agatagtgtg    1560
gaggatttgt ttgtgtctag actaaagaaa gagcatccta atttgtccaa tgctgacgtg    1620
cgattaatga tgctgttgcg tttaaagtta tcgcaaaaga ctttagcatc tatctattgt    1680
gtgagcgaga aagctatcaa gcaaaagttg ttcttgtata aggataaagt aggcattaaa    1740
aatgagcatt tttcgcttcg taactacata gaaaacttct ag                      1782

<210> SEQ ID NO 54
<211> LENGTH: 1395
<212> TYPE: DNA
<213> ORGANISM: Prevotella copri

<400> SEQUENCE: 54
atgcagaatg aaagtcaaaa tatagaatat aaggaatcat ggcgtgatga atatctgaaa      60
tggatatgtg gtttcgccaa tgcccaaggt ggacgtattt atatcggtgt aaacgaccag     120
aaagaagtaa tcggtttatc tgatgccaaa cgattgttgg aagatattcc taacaagata     180
gttaattatc tgggcatcgt agaagatgta aaccttctta tggaaggtga taagagtac      240 atagagattg tggtctcacc aagtaatatg ccgatagcct ataaaggtac gtatcattat     300
cgtagtggtt ctaccaagca agaactcaaa gggcttgctt tgcagcaatt cattatggag     360
aagatgggtc attcatggga cgatattcct gtttatggtg ctactcttga tgacatagac     420
cgtaatgcga ttgactattt tttgcaatgt agcatcaagg caggtcgtat ggatgaatca     480
gagactaatt cgtcgaccga agatgtattg cgtaatcttg gcttgtttac cagggaaggt     540
gaattgaaaa atgctgccat cttgcttttc ggaaagcatg ttggtcagtt cttcccatct     600
gcggtattca agataggacg ttttcataca gatgagagcg atttgattat tcaggatgtg     660
atagaaggca acctgattca aatggcaagt cgagtgatgg aagtactccg aaccaagtat     720
ctgctttcgc ctattcacta tgagggattg cagcgcatag agcagctgga gattcctgat     780
aaggcattac gagagttgat atacaatgcc atttcgcata aggcttatac cggccctgcc     840
atccagatgc gtatctacga ccgcagtata gaattgtgga attatggatt gttgccaaaa     900
gagttgactc ctgcagcttt gttgcagaag cattcttctt atcctcgtaa ccataatatt     960
gccaatgttt tttacaaagc aggctttgtg gagtcatggg acgtggctt caagaagatt    1020 gccgaggagt ttgaacgtgc cagcttgcca ttgccaacaa tagaagaaaa tggaggtggc    1080
gtgatggcga taattcaacg aaagacggta gatgacgtta tcgcagcgcg tgacgggaat    1140
gtcggtaata tgtcggtaac aaatgtcggt aatgtgtcgg taaggaaact gtctggtcgt    1200
cagcgaaata tcatttctat gattgaggaa atccttttg taacagctaa ggaaatgtcg    1260
gtaacaatgt cggtaacgaa acgtaccata gaacgtaatt tgtctgtgtt gcaaaaagcg    1320
ggaataataa ggcatgaagg aagagtgaat gccggtgttt gggtgatact tgaacaagga    1380
aatatgaatt cttaa                                                    1395

<210> SEQ ID NO 55
<211> LENGTH: 26
<212> TYPE: DNA
<213> ORGANISM: Artificial Sequence
```

```
<220> FEATURE:
<223> OTHER INFORMATION: Synthetic oligonucleotide

<400> SEQUENCE: 55
atgcagaatg aaagtcaaaa tataga                                          26

<210> SEQ ID NO 56
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 56
ttaagaattc atatttcctt gttcaa                                          26

<210> SEQ ID NO 57
<211> LENGTH: 1050
<212> TYPE: DNA
<213> ORGANISM: Prevotella copri

<400> SEQUENCE: 57
atgagacagg caatattggt agaaccaaag catatcgaat tcaaggaagt agcagaacca     60
aaggcagcag acttaactgc tcatcaggtt ctcgtcaaca tcaagcgcat cggcatctgc    120
ggtagcgaga ttcactctta ccacggtctt cacccagcca ccttctaccc agtggttcag    180
ggacatgagt actcaggagt ggttatggct gtaggcagcg aagttaccgt ctgcaagcct    240
ggcgaccata tcaccgctcg cccacagttg gtttgcggca agtgcaaccc ttgcaagcgc    300
ggacagtata atgtttgtga gcacctgcgt gttcaggctt ccaggcaga tggtgcagca     360 caggatttct ttgtagtaga tgacgaccgc gtggctaagt tgccggaagg catgagcctt    420
gactacggtg ccatgattga gccttcagcc gttggtgccc atgccagcaa ccgcaccgat    480
gtgaagggta agaatgtagt tgtgagcggt gcaggaacca tcggcaacct catagcccag    540
ttctgcattg cccgtggcgc caagaatgta ctcattaccg atgtaagcga cctccgcctg    600
gctaaggctc gcgaatgcgg catcaagcac accctcaaca tcaccaagaa gaccttgaag    660
gaggcagccc aggaactttt cggtgaggaa ggctatcagg taggtttcga ggtagcaggt    720
gtagaagttt ccatccgttc gctgatggag accatcgaga aggtagcga catcgtggtt     780 gtggcagtct ttgccaagga cccagccctc agcatgttct atctgggcga gcatgagttg    840
agactcatcg gttcaatgat gtatcgccac gaagattatc tcacagccat cgattacgta    900
agcaagggca tcgtcaacct caagccactc gtaagcaacc gttttgcctt cgaagaatac    960
gatgatgcct acaagtttat cgacactcat cgcgaaacca gcatgaaggt tctcatcgat   1020
ttcgaacaga aacctggaga gaagaagtaa                                    1050

<210> SEQ ID NO 58
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 58
atgagacagg caatattggt agaacc                                          26

<210> SEQ ID NO 59
<211> LENGTH: 26
<212> TYPE: DNA
```

<213> ORGANISM: Artificial Sequence
<220> FEATURE:
<223> OTHER INFORMATION: Synthetic oligonucleotide

<400> SEQUENCE: 59
ttacttcttc tctccaggtt tctgtt                                          26

<210> SEQ ID NO 60
<211> LENGTH: 735
<212> TYPE: DNA
<213> ORGANISM: Prevotella copri

<400> SEQUENCE: 60
atgaaaagaa ttgtagttat tgttttgatg atggctgctt gcctgggaaa tgcccaggca     60
cagctccatc tgaaagccaa cgtgcagaac aatcatctgt ggcgtggcat ggaagtttcc    120
gacggcatcg tcctcctcac cgacctgagc tatacgatgg ccaatgacca cgttaccgtg    180
ggactttggg gtggctgcaa ctcggaaggc tcctacaagg agtttaatca ttatctgaat    240
ctgaaggctg gcggttgggg attcgccctg tgggacacct acaacttctc ccctggcgcc    300
agctataata ataaggaata ctggaactac tctgctcata ccaccggccg attcctcgat    360
gctacattaa gctaccggtt tcagtacgag aagtttccac tgctcctgag ttggtcaacg    420
gtagtcttcg gacgcgaccg caacagcaac aacacgaagc agaaatattc caccttcgcc    480
tatgcggaat atcctatcta tcagaaggat ggctggaagg tagatgcagg agttggtgga    540
gccttcgccc tgaacagagc tggcgaggat gcccacttct tcggaaccac ggcaggcatc    600
gttcacgtat cgctgcaagc cacccacgac ctcaagctcg gcaactacac cgttccggtt    660
tatgccaagg gcatgtggaa tccgcagagc aacgagagtt atttccagat tggagcagaa    720
atcatccgct tctaa                                                     735

<210> SEQ ID NO 61
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 61
atgaaaagaa ttgtagttat tgtttt                                          26

<210> SEQ ID NO 62
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 62
ttagaagcgg atgatttctg ctccaa                                          26

<210> SEQ ID NO 63
<211> LENGTH: 2841
<212> TYPE: DNA
<213> ORGANISM: Prevotella copri

<400> SEQUENCE: 63
ttgtataatt ttaaaaaaga aaaatttatg aagaatcagt tttggggatt attccttctc     60
tctttgtttc cagcttcatt gttcgctcag actgtggagc aggacacttc cgtgcgacag    120
ggcaagttga agaatggact gacttactat atacgacata taataaaga ggcaggcctt    180

```
gccgatttct atattgccca gcgcgtaggt tccatccttg aggaaccccg tcagcgtgga      240
ctggctcatt ttctggagca catggctttc aatggtacca agcatttccc tggcaagggg      300
aagaagttgg gaatcgtgcc ttggtgtgaa accataggtg tcaagtttgg agccaacctg      360
aatgcctata catctgtaga tcagacagtc tatcacatcg ggtctgcccc tgtcaagcgt      420
gagggcatta ttgattcgtg tcttctggta ctcaacgact ggagccagta tatcaatctc      480
gaacctaagg agatagacaa ggaacgtggt gttattcatg aagagtggag aaaccggcgt      540
accggtatgg ccatgcagcg catgatggag aatgtgatgc caaaaatcta caagggaagc      600
aaatatgaag attgtatgcc tatcggcagt atggatgttt tgataacttt tccttacaga      660
gatttgcgcg actattatca gaagtggtac aggcctgatc ttcaggccat cgtagttgtg      720
ggcgacttcg atgtggatat gatggagaag aaaatccaga aacttttcgg taagatcaaa      780
gcccataaga atcctgcaga gcgtgtctat tatcccgtaa ataacaacga caagatgata      840
gttgccattg agaaggacaa ggagcagcct attatcatcg gccatctcta catgaaaacc      900
gatgccactc ctgacagcga aaagagccag gtaaagtatc agcgtgatga ctatgtaagc      960
ggactcatca cttacatgct caatggccgt ctctcagaaa agaaacaggt ggcaaatcct     1020
ccattcatga gtgctaccgt aaggaatggt gcttttttg tttcccgtac caaggatgcc     1080
ttcagtatga gcatcagctg caagcaggat cacgtactcg gtggtatcta cgaggctgtg     1140
ggtgaaatag agcgtgcccg ccagcatggt tttacagaga gtgaactgga acgtgccaag     1200
aaactctatc tcaatgcagc agaacgaaaa ctgaagatgg agaaggatta tcgcaacgcc     1260
cattacgtaa gccagtgtgt ggatcatttc cttgaaggag agcctatcct tactccagcc     1320
tataatctgc aactggtaaa gcagtttgat ggtgaagtaa ccctggctga ggttaatcag     1380
tctgtaggta acatcattac ggataaaaac caggtatttg tgatgtatgg ccctgataag     1440
gaaggatttg ttattccttc agaatcagaa atagaagcta cggtacttgc tgcccagaaa     1500
aagcaatatg aaccgtatca ggaggaaaag attccttcta cgttgatgtc tgccttgcca     1560
aaaccgggca agattgtgtc tgaaaaacca tacggcaagt ttgggatgac agagattacg     1620
ctcagtaatg gtatgaaggt ttacgtaaaa cctaccgact atcaggcaga ccaggtaatg     1680
atgagcatgc gcgctgaagg tggaacctca ctttacggaa atgaggatat tcctaatttc     1740
tctctcttga caagtgccat cacagaagcg ggtgtaggcg acttttcagc tactgctttg     1800
cgtaaggctt tggcaggaaa gtcaatcagg ctgactccat ccatcagtag tgaaggccag     1860
cgtatagcag gctcatcttc tgtaaaggat atggaaacca tgctccagct ggcacacctt     1920
tatttcatgg cacccgtaa agacagtgtg gcatttgagg gtttgaagaa tcgaacgctg     1980
tcatttctga aaaccgtaa tgcaagttcc aaggtggttt acaatgactc cctttctgcc     2040
gttctctatg accataaacct gcgtatggct cctgtcaccg gtgaggttct tgccaaggct     2100
gattacgggc gcattatgga aatctatcgt gaacgcttca gcgatgctag caatttcaaa     2160
accgttttca tcggaaagat agacatggca gaacttcgtc ctttactctg tcagtatctg     2220
gctaccttgc cttcgaccta taagaaggag gagacagaca agaaaaacgt tccgcagatt     2280
gttatgaaga acgaaacggt gaagtttgtt catcagcagg aaacaccgct tgccaacgtg     2340
agcgtgttct atacgggcaa cgtaccgttc tcaccaaaga acgatctggt gctggatgtc     2400
ctgacccgcg tattgcagat agcctataca gattctgtaa gagaggagaa gggaggtacc     2460
tatggagtag gagtcagttt caaccttgag aaggatgccc ttccaaatgc cttacttcgc     2520
```

-continued

| | |
|---|---|
| attacctaca agagtgatcc gaaacgttat gaagaactga atcctattat ctaccagcaa | 2580 |
| cttcagaaca tcgcagataa ggggccttta gccagcagta tggataaggt gaagaaatat | 2640 |
| ctgaaaaaac aataccagca gatgattatc accaacgact actggagtta tgttatctgg | 2700 |
| catgagttgg atgatgatgc cgattttgat aaagattact ataagatggt ggattctctt | 2760 |
| acttctgaag aggtgcagca gatggcacag actctgctca aacagaatca tcggatagag | 2820 |
| gtaacaatgc tgtctgagta a | 2841 |

<210> SEQ ID NO 64
<211> LENGTH: 477
<212> TYPE: DNA
<213> ORGANISM: Prevotella copri

<400> SEQUENCE: 64

| | |
|---|---|
| atgaaggtaa agaatagtag aatggaaacc ctgaagatgc ttatctcaag tcaagagtta | 60 |
| agttcacagg aagaagtttt gaaggccttg tcaaaagaag gttataagct tacgcaagcc | 120 |
| actttaagcc gcgacttgaa acaactgaaa gttgccaaag ccgcctctat gaatggtaaa | 180 |
| tatgtatatg tactccctaa tgaaaccatg tacaagcgag tttccaatcc tcgttcgctc | 240 |
| aaagaaatga tgatgacccc aggatttcta tccatcaact tttctggaaa catgattgtc | 300 |
| atcaagactc gtccgggtta tgccagcagt attgcatata acattgacaa tcatgacatt | 360 |
| cctgaaatct tgggtacaat tgctggagat gacacgattt tcctggtaaa gaagaagat | 420 |
| gcttctgagg aagcacttct gaaatcactc gcaaatgcca ttccagaact gaagtaa | 477 |

<210> SEQ ID NO 65
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 65

| | |
|---|---|
| atgaaggtaa agaatagtag aatgga | 26 |

<210> SEQ ID NO 66
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 66

| | |
|---|---|
| ttacttcagt tctggaatgg catttg | 26 |

<210> SEQ ID NO 67
<211> LENGTH: 387
<212> TYPE: DNA
<213> ORGANISM: Prevotella copri
<220> FEATURE:
<221> NAME/KEY: misc_feature
<222> LOCATION: (143)..(161)
<223> OTHER INFORMATION: n is adenine or guanine or cytosine or thymidine/uracil

<400> SEQUENCE: 67

| | |
|---|---|
| ttgaagaggc ttcagaagca ccggcttcca aagcaccagt ttcagaagca ccagccttca | 60 |
| agccagcagt ttccaaagca caaccatcag ctccgaaatc ctgcagtctg cagcattcta | 120 |
| tttccaccct gtcgcgaaac ggnnnnnnnn nnnnnnnnnn nctctatctc aaactgttta | 180 |

```
aatcgaaaat tacccataaa ttcttctgtc tctttacaga agaaaacgaa tgcgccgccg    240
atttatttta tcgcaagcag cagaaattgc cacttccacc tgcaaaagca gctacttaca    300
tctataaaaa cgggtactaa atatatagaa aaagcaattt tattattaaa taatctatca    360
tcttccacga tatttcacaa aaaatga                                        387
```

```
<210> SEQ ID NO 68
<211> LENGTH: 366
<212> TYPE: DNA
<213> ORGANISM: Prevotella copri

<400> SEQUENCE: 68
atgacccggt atcttgcggg ctttcttacc cgatacccta ctgtaccgtc catcctcctc     60
ttccggtttc agttcgatac ccaggaggtt tctccacgta ggctccaggg tatcacagaa    120
gtaatgctcc ttgtccaact tcgccatatc aaagctgtgc tcaaagatac gcttgtcgcc    180
aattttcaca cccgaacgcc aggtacgctt cacgtcctta tcactcagga tataaagatg    240
acctatcgta taagtcttct tttttgctat tctttttact actatttcca taactcaaac    300
tctattaaga ttctaaaatt tttacctctt taccatcctt gcggttacgt agcttttcaa    360
aactga                                                               366
```

```
<210> SEQ ID NO 69
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 69
atgacccggt atcttgcggg ctttct                                          26
```

```
<210> SEQ ID NO 70
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 70
tcagttttga aaagctacgt aaccgc                                          26
```

```
<210> SEQ ID NO 71
<211> LENGTH: 663
<212> TYPE: DNA
<213> ORGANISM: Prevotella copri
<220> FEATURE:
<221> NAME/KEY: misc_feature
<222> LOCATION: (54)..(75)
<223> OTHER INFORMATION: n is adenine or guanine or cytosine or
      thymidine/uracil

<400> SEQUENCE: 71
gtgcaaacgt ttgcacaaag aaatgtagcc ttttgaaac ttttttcttgc ttcnnnnnnn     60 nnnnnnnnnn nnnnnaaaag taaagatatg atgaagcaaa cattcataaa atcagcaatg    120
ttgctgctgc tgatcctttc aacggcaacg acgcgagcgc aggaggtcgc tctgaagacc    180
aacttactgg gatgggcttc tacatctgcc aacgccggca tagaaatcgg cacgggcaag    240
aaaacaacct tccaactctt cggaaccctg aaccccctgga agttctcggg cgacaagaag    300
atgagattct ggaatgttat gccagaatac agatggtaca cctgccagaa gtttggaggc    360
```

```
catttcttcg gaatccatgc cttaggcggt gaatacaaca ttaaaaacat tgacatgccc    420
ttcggcatcc tgccgaaaac tctggagggc aggcactatg aaggctggta tgtaggtgga    480
ggccttacct acggctatca gtggttgctt aataagcacc tcaatttcga aggctctatc    540
ggtttgggat atgcctacag tccttacaag ctttacggac gatgcgaaaa atgtctcgac    600
aaagaccacc gcaactatgt gggccctaca aaagccgcac tatctctcat atacgtgttc    660
taa                                                                 663

<210> SEQ ID NO 72
<211> LENGTH: 561
<212> TYPE: DNA
<213> ORGANISM: Prevotella copri

<400> SEQUENCE: 72
atggaaatag tagtaaaaag aatagcaaag aagaagactt atacgatagg tcatctttat     60
atcctgaacg ataaggatgt gaaacgtacc tggcgttcag gggtaaaaat aggcgacaag    120
cgtatctttg agcacagctt cgataaggcg aagttggaca aggagcatta cttctgtgat    180
accctggagc ctacgtggag aaacctcctg ggtatcgaac tgaaaccgga agaggaggat    240
ggacggtaca gcagggtatc gggtaagaaa gcccgcaaga taccgggtca tacggcgata    300
ccggaaggct cgtatcctgt tgttatctcg aaatcgccaa ggtttaagaa gtggcttccg    360
ctggtgcagg tgttcctga ttttgagggc atccgcattc atgccggtaa ttatcctgat    420
gatacgcagg gctgcattct ggtaggtgaa aataaattac agggtgccgt ctttaattcc    480
cgcatctggc tgcacaggct catgaatgcc attaccgcag caagggaacg ggaggagagc    540
gtttggatta caatcattta a                                             561

<210> SEQ ID NO 73
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 73
atggaaatag tagtaaaaag aatagc                                         26

<210> SEQ ID NO 74
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 74
ttaaatgatt gtaatccaaa cgctct                                         26

<210> SEQ ID NO 75
<211> LENGTH: 558
<212> TYPE: DNA
<213> ORGANISM: Prevotella copri
<220> FEATURE:
<221> NAME/KEY: misc_feature
<222> LOCATION: (200)..(239)
<223> OTHER INFORMATION: n is adenine or guanine or cytosine or
      thymidine/uracil

<400> SEQUENCE: 75
ttgctggcat ccctgttgct gatgctcgta gcgacgctta cttcatgcga gaagttttcg     60
```

```
attgacgaaa caaccggaaa atcacatgat gcaaacgcca atgtaacgat tcatgtgcag      120
aaagtagaaa acaccaatct gttgacgacc aaagctgccg acaagcagat tgccctgggc      180
gatgtgtgct ccagactgan nnnnnnnnnn nnnnnnnnnn nnnnnnnnnn nnnnnnnnng      240
ctctatcagc gcacccgaga aggtgaagtt tgcaagcaac aaacttaccg acaccttttta     300 ttattacggc aggttgagcg taaacgaaga gggcgccacc acagacatca acctgaggcg      360
agcagttggc gccttcaagg tacatattac cgacgaaaac attcccgaag aaatcaggag      420
catcaagttc tattataccg gcggcagcag caccctggat gcaaccaccg gattcggctg      480
cgtgaacagc cgtcagaccg agaatttcag tatgaaagat ggcagcagag actttaccgt      540
ctacaccttc ccacatga                                                    558
```

```
<210> SEQ ID NO 76
<211> LENGTH: 468
<212> TYPE: DNA
<213> ORGANISM: Prevotella copri

<400> SEQUENCE: 76
```

```
gtggcttccg cgtacgaaat cagccatctc caggttctct atcagattag gcgtaatctt      60
catgatttcg ttctgatgag aagcacgaaa gttgatgtcg taataaagaa tggcgccgtg     120
ctccttcgca tactccagga agccggcaac ctgaggacgg accacaggat tcagagcgaa     180
gaacgaaccg aagagcacga tgtcgccagg attgatttcc ggtgtggcaa actccagctg     240
gtcgtgagga tgatccttgt agaagatgta gtcggcattg ttgttctcgt cgaggaaagc     300
cagcgagagc ggcgacttcg attccggaaa gatgctcaca ttgtcagcat tcaccccatt     360
atctctcaaa aactgaatca catactctcc tatgcggtcg ttgcccgcct cgctgataaa     420
cgaagcattt acacccgcac ggcccaacga gatgactgca ttgaatga                  468
```

```
<210> SEQ ID NO 77
<211> LENGTH: 465
<212> TYPE: DNA
<213> ORGANISM: Prevotella copri
<220> FEATURE:
<221> NAME/KEY: misc_feature
<222> LOCATION: (106)..(129)
<223> OTHER INFORMATION: n is adenine or guanine or cytosine or
      thymidine/uracil
<220> FEATURE:
<221> NAME/KEY: misc_feature
<222> LOCATION: (265)..(265)
<223> OTHER INFORMATION: n is adenine or guanine or cytosine or
      thymidine/uracil

<400> SEQUENCE: 77
```

```
atgcagggca cagagcgagc ggttcagctc ctgggctgtg ataccgagtt ccttcgcaat      60
ctgcgtagta gtgaagcagg aaacggaatc gagcacgtta tcgctnnnnn nnnnnnnnnn     120
nnnnnnnnna tcggccgtaa cccagttctt gaacttcacg gcagtagaaa gcttagagcc     180
gagaaccaaa gcatagaaac cgctctcgtt gacatagagc atcagagtac gacgcatcgc     240
cgaggttcca tccttcttca gaccncagca tcattcgctc tcttatatcc cagtacatta     300
cagagatcct ttgcacagaa caatggctcc ccattttcat cggtcaaggt acgaaccttt     360
ccgaattctg attttcaaa cacgacagca attgctgcct tcttatccat ttctactttta    420 tttgtattaa ctgactttac cataataatc ttttaaaaa aataa                      465
```

```
<210> SEQ ID NO 78
<211> LENGTH: 26
```

```
<212> TYPE: DNA
<213> ORGANISM: Artificial Sequence
<220> FEATURE:
<223> OTHER INFORMATION: Synthetic oligonucleotide

<400> SEQUENCE: 78
atgcagggca cagagcgagc ggttca                                          26

<210> SEQ ID NO 79
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 79 ttatttttt aaaaagatta ttatgg                                           26

<210> SEQ ID NO 80
<211> LENGTH: 369
<212> TYPE: DNA
<213> ORGANISM: Prevotella copri
<220> FEATURE:
<221> NAME/KEY: misc_feature
<222> LOCATION: (230)..(244)
<223> OTHER INFORMATION: n is adenine or guanine or cytosine or
      thymidine/uracil
<220> FEATURE:
<221> NAME/KEY: misc_feature
<222> LOCATION: (324)..(333)
<223> OTHER INFORMATION: n is adenine or guanine or cytosine or
      thymidine/uracil

<400> SEQUENCE: 80
atgatatttc tcatcgcccc ttacaaccac cgtatcacgt ttaatcagcg tattctgatt      60
cagcgccacg gaagcatggt tgtggatgaa ctgctgcaaa taagacttat cttccgtctt    120
caccagctta accacatccc cattctgcac tttaaactgg aaaatatgct cagcctgttt    180
tacaatcgga tattttgcaa gattagcacc cttcattaca agcgtatcgn nnnnnnnnn    240 nnnntcactt cctgttgctt ttcgaccttc tgcccacaag caacaagagt caagatacaa    300
ctgagcagcc ataaattaac tatnnnnnnn nnnggccatt ttattccgat agtaggatca    360
tcccaatga                                                            369

<210> SEQ ID NO 81
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 81
atgatatttc tcatcgcccc ttacaa                                          26

<210> SEQ ID NO 82
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 82
tcattgggat gatcctacta tcggaa                                          26

<210> SEQ ID NO 83
```

```
<211> LENGTH: 351
<212> TYPE: DNA
<213> ORGANISM: Prevotella copri
<220> FEATURE:
<221> NAME/KEY: misc_feature
<222> LOCATION: (63)..(78)
<223> OTHER INFORMATION: n is adenine or guanine or cytosine or
      thymidine/uracil
<220> FEATURE:
<221> NAME/KEY: misc_feature
<222> LOCATION: (259)..(288)
<223> OTHER INFORMATION: n is adenine or guanine or cytosine or
      thymidine/uracil

<400> SEQUENCE: 83
atgcgacaag agcggataag tcttgttacg caccagtttg acaggtgtac ctttgataaa     60
ctnnnnnnnn nnnnnnnnct ccgtaaaact ctgatgatat cccgacctga actcccctac   120
ttcctgagcc gtaggattac ccacatagtg aataggataa cggtgcttct tttcgaagaa   180
cggcacctcg aatggcaaga tagagaagag ttcaacgata tcacgtttaa tgctgcggat   240
ccgccactcc ttccatgcnn nnnnnnnnnn nnnnnnnnnn nnnnnnnntc cactagcctc   300
gcctactatc aggtaatact tcataattca aaattcttta accaatcata a             351

<210> SEQ ID NO 84
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 84
atgcgacaag agcggataag tcttgt                                          26

<210> SEQ ID NO 85
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 85
ttatgattgg ttaaagaatt ttgaat                                          26
```